US012187708B2

(12) United States Patent
Blasi et al.

(10) Patent No.: US 12,187,708 B2
(45) Date of Patent: *Jan. 7, 2025

(54) NEAR-INFRARED CYANINE DYES AND CONJUGATES THEREOF

(71) Applicant: BRACCO IMAGING S.P.A., Milan (IT)

(72) Inventors: Francesco Blasi, Rivarolo Canavese (IT); Federica Buonsanti, Turin (IT); Federico Crivellin, Grugliasco (IT); Andrea Ferraris, Genoa (IT); Laura Orio, Turin (IT); Lorena Pizzuto, San Francesco al Campo (IT); Roberta Napolitano, Albiano d'Ivrea (IT); Giovanni Valbusa, Stresa (IT)

(73) Assignee: BRACCO IMAGING S.P.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 18/388,604

(22) Filed: Nov. 10, 2023

(65) Prior Publication Data

US 2024/0083880 A1 Mar. 14, 2024

Related U.S. Application Data

(63) Continuation of application No. 18/010,905, filed as application No. PCT/EP2021/066920 on Jun. 22, 2021.

(30) Foreign Application Priority Data

Jun. 23, 2020 (EP) ..................................... 20181771

(51) Int. Cl.
*C07D 403/10* (2006.01)
*C07D 403/14* (2006.01)
*C09B 23/01* (2006.01)

(52) U.S. Cl.
CPC ......... *C07D 403/10* (2013.01); *C07D 403/14* (2013.01); *C09B 23/0066* (2013.01); *C09B 23/0075* (2013.01)

(58) Field of Classification Search
CPC .............. C07D 403/10; C07D 403/14; C07B 23/0066; C07B 23/0075; C09B 23/0066; C09B 23/0075

See application file for complete search history.

(56) References Cited

U.S. PATENT DOCUMENTS 11,851,421 B2 * 12/2023 Blasi .................... C07D 403/14

FOREIGN PATENT DOCUMENTS

| CA | 2368490 | A1 | 10/2000 |
|---|---|---|---|
| CN | 1351505 | A | 5/2002 |
| EP | 3636635 | A1 | 4/2020 |
| WO | 0224815 | A1 | 3/2002 |
| WO | 2004065491 | A1 | 8/2004 |
| WO | 2007136996 | A1 | 11/2007 |
| WO | 2015114171 | A1 | 8/2015 |

OTHER PUBLICATIONS

Achilefu, S. et. al., "Synthesis, In Vitro Receptor Binding, and In Vivo Evaluation of Fluorescein and Carbocyanine Peptide-Based Optical Contrast Agents," J. Med. Chem., 45:2003-2015 (2002).
Benešová, M. et al., "Preclinical Evaluation of a Tailor-Made DOTA-Conjugated PSMA Inhibitor with Optimized Linker Moiety for Imaging and Endoradiotherapy of Prostate Cancer," J. Nucl. Med., 56(6):914-20 (2015).
Capasso, D. et. al., "RGDechi-hCit: avB3 selective pro-apoptotic peptide as potential carrier for drug delivery into melanoma metastatic cells," PlosOne pp. 1-10 (2014).
Capozza, M. et. al., "Photoacoustic imaging of integrin-overexpressing tumors using a novel ICG-based contrast agent in mice," Photoacoustics, 11:36-45 (2018).
Cherrick, G.R., et al., "Indocyanine Green: Observations on Its Physical Properties, Plasma Decay, and Hepatic Extraction," J. Clin. Invest., 39:592-600 (1960).
Fidel, J. et al., "Preclinical Validation of the Utility of BLZ-100 in Providing Fluorescence Contrast for Imaging Spontaneous Solid Tumors," Cancer Res., 75:4283-4291 (2015).
Greene, T.W., "Protective groups in organic synthesis," Chapter 5, pp. 533-646, John Wiley & Sons, Inc. (2007).
Hoogstins, C. et al., "A Novel Tumor-Specific Agent for Intraoperative Near-Infrared Fluorescence Imaging: A Translational Study in Healthy Volunteers and Patients with Ovarian Cancer," Clin. Cancer Res., 22:2929-2938 (2016).
International Search Report and Written Opinion for PCT/EP2021/066920, mailed Aug. 30, 2021.
Kapp, T.G. et. al., "A Comprehensive Evaluation of the Activity and Selectivity Profile of Ligands for RGD-binding Integrins," Scientific Reports pp. 1-13 (2017).
Li, Z. et al., "Identification and characterization of a novel peptide ligand of epidermal growth factor receptor for targeted delivery of therapeutics," FASEB Journal, 19:1978-85 (2005).
Mujumdar, R.B. et. al., "Cyanine Dye Labeling Reagents: Sulfoindocyanine Succinimidyl Esters," Bioconjugate Chem. 4(2):105-111 (1993).
Onda, N. et. al., "Preferential tumor cellular uptake and retention of indocyanine green for in vivo tumor imaging," Int J Cancer, 139:673-682 (2016).
Tummers, Q. et. al., "The Value of Intraoperative Near-Infrared Fluorescence Imaging Based on Enhanced Permeability and Retention of Indocyanine Green: Feasibility and False-Positives in Ovarian Cancer," PlosOne, 10(6):e0129766 (2015).

(Continued)

*Primary Examiner* — Rebecca L Anderson
(74) *Attorney, Agent, or Firm* — VIVICAR Law, PLLC

(57) ABSTRACT

The present invention relates to the field of optical imaging. More particularly, it relates to compounds of the cyanine family with near-infrared emission characterized by improved physico-chemical and biological properties and to conjugates with biological ligands thereof. The invention also relates to the use of these compounds as optical diagnostic agents in imaging or therapy of solid tumors, to the methods for their preparation and to the compositions comprising them.

9 Claims, No Drawings

(56) References Cited

OTHER PUBLICATIONS

Vendrell, M. et al., "Synthesis and characterization of a cell-permeable near-infrared fluorescent deoxyglucose analogue for cancer cell imaging", Organic & Biomolecular Chemistry, 9:4760-4762 (2011).
Wada, H. et al., "Multivalent mannose-decorated NIR nanoprobes for targeting pan lymph nodes," Chemical Engeneering Journal, 340:51-57 (2018).
Wichert, M. et. al., "Dual-display of small molecules enables the discovery of ligand pairs and facilitates affinity maturation," Nature Chem. pp. 1-9 (2015).
Williams, T.M. et al., "Peptide Ligands for Targeting the Extracellular Domain of EGFR: Comparison Between Linear and Cyclic Peptides," Chem. Biol. Drug Des. 91:605-619 (2018).
Yamana, T. et al., "Studies on the Stability of Amides. I. Hydrolysis Mechanism of N-substituted Aliphatic Amides," Chem. Pharm. Bull., 20(5):881-891 (1972).

* cited by examiner

NEAR-INFRARED CYANINE DYES AND CONJUGATES THEREOF

FIELD OF THE INVENTION

The present invention relates to the field of optical imaging. More particularly, it relates to compounds of the cyanine family with near-infrared emission characterized by improved physico-chemical and biological properties and to conjugates with biological ligands thereof. The invention also relates to the use of these compounds as optical diagnostic agents in imaging or therapy of solid tumors, to the methods for their preparation and to the compositions comprising them.

BACKGROUND ART

Dyes are chemical entities that absorb photons of a specific wavelength upon light excitation and re-emit some of that energy, depending on quantum efficiency, usually at a longer wavelength. Particularly, cyanine dyes are fluorescent organic molecules characterized by a delocalized electron system that spans over a polymethine bridge and is confined between two nitrogen atoms. Some of them, having favourable optical properties, low toxicity and good solubility in aqueous media, can be used as contrast agents for biomedical imaging. Cyanine dyes emitting in the near-infrared region (700-900 nm) are particularly useful for biomedical imaging applications due to the higher penetration depth compared to dyes with fluorescence emission in the visible spectrum.

Among the near-infrared dyes used for biomedical imaging, Indocyanine green (ICG) is the only medicinal product currently approved for human use. ICG is routinely used to assess tissue perfusion and for angiographic applications due to the strong binding to plasma protein (blood pool effect) and rapid clearance of the unbound fraction by the liver (Cherrick et al., J Clin Invest 1960; 39(4): 592-600). Furthermore, ICG is also tested as investigational medicinal product for tumor imaging during diagnostic and interventional (fluorescence-guided surgery) procedures. ICG distributes and accumulates in tumor tissues by a combination of passive diffusion and enhanced permeability and retention (EPR) effect (Onda N. et al., Int J Cancer 2016; 139, 673-682). False positives are common clinical findings associated with the use of ICG for tumor imaging due to the non-specific accumulation properties (Tummers Q. et al., PlosOne 2015; 10(6): e0129766).

Further contrast agents for near-infrared imaging are under development which exploit the use of a dye conjugated to a carrier moiety (i.e., biomolecule), targeting an overexpressed tumor epitope, to improve sensitivity and specificity of detection (Achilefu S. et al, J Med Chem 2002; 45, 2003-2015). For instance, ICG and S0456 are examples of near-infrared dyes that have been conjugated to tumor-targeting moieties and are currently tested in clinical trials for intraoperative tumor detection (Fidel J. et al., Cancer Res. 2015; 15; 75(20): 4283-4291; Hogstins C. et al., Clin Cancer Res 2016; 22(12); 2929-38).

Despite several efforts to find suitable imaging agents, there is still the need to find improved dyes endowed with optimal solubility and low aggregation in aqeous media, high fluorescence efficiency and optimal biological properties. The biological properties of the dye, especially the binding affinity to plasma proteins such as albumin, may strongly impact distribution and tissue accumulation once administered into a living organism. For instance, dyes with high binding affinity to human albumin are sequestered in the plasma compartment after intravenous administration, and have low tissue extravasation rate which strongly limits their diagnostic applications. Furthermore, the biological properties of the dye may influence the tissue distribution of conjugates composed of the dye itself and a biomolecule targeting a biological epitope on a pathological tissue. Near-infrared dyes endowed with low binding affinity for human serum albumin and non-specific accumulation would be preferable for applications in living organisms. This need is paramount when the dye is conjugated to a biomolecule that specifically binds a molecular epitope or a pathologic tissue (e.g. a tumor). The present invention addresses these and other needs.

WO2002/024815 and WO2007/136996 in the name of Li-Cor Inc. and WO2004/065491 in the name of Schering AG report stable cyanine dyes useful for optical imaging applications and characterized by high solubility in aqueous media and functional groups for direct conjugation with biomolecules. However, no teachings are therein provided about how to obtain dyes with optimal biological properties.

WO2015/114171 discloses small molecule targeted drug conjugates for delivery of drugs to inhibit the cancer cells. In particular, it reports the IRDye 750 conjugate "C6" used for flow cytometry analysis and in vivo imaging of tumors.

Wada H. et al, Chemical Engineering Journal 2018, 340 (3): 51-57 discloses NIR fluorescent nanoprobes using mannose-conjugated ZW800-1 derivatives for intraoperative pan lymph nodes mapping and real-time optical imaging.

Vendrell M. et al, Organic & Biomolecular Chemistry 2011, 9 (13): 4760-4762 reports a NIR fluorescent deoxyglucose analogue CyNE 2-DG which showed a preferential uptake in cancer cells and was validated as optical agent in imaging of tumors.

Despite several efforts to find suitable imaging agents, there is still the need to find improved dyes endowed with optimal stability and fluorescence efficiency, as well as optimal physicochemical and biological properties, and designed for optical imaging of living organisms. This need is paramount particularly when the dye is conjugated to a biomolecule that specifically binds a molecular epitope or a pathologic tissue (e.g. a tumor). The present invention addresses these and other needs.

SUMMARY OF THE INVENTION

Generally, object of the present invention is to provide new cyanine dyes, or their corresponding conjugates to binding moieties, useful as contrast medium for optical imaging and aimed at solving the above mentioned issues.

The new cyanine derivatives described herein are surprisingly endowed with remarkable optical properties and high solubility in aqeous media. Surprisingly, it has been found that the compounds of the invention have a very low binding affinity for human albumin compared to near-infrared dyes known in the prior art, which is particularly advantageous when these compounds are used after intravenous administration; said low affinity prevents the sequestration of the compounds in the plasma compartment by the large proteins present in the blood, such as albumin, and the consequent reduction of the fraction of free dye available for efficient extravasation and distribution in the extracellular space.

The new cyanine dyes can be conveniently conjugated to suitable targeting moieties through suitable functional groups acting as binding sites, thus providing very specific and sensitive contrast agents for molecular imaging. This low albumin binding affinity of the compounds of the invention is particularly important in case of dyes-conjugates, since only their free fraction (not bound to albumin) can efficiently interact with the molecular target.

A further aspect of the invention relates to such dyes as diagnostic agents, in particular for use in optical imaging of a human or animal organ or tissue, for use in a method of optical imaging, wherein the imaging is a tomographic imaging of organs, monitoring of organ functions including angiography, tissue perfusion imaging, urinary tract imaging, bile duct imaging, nerve imaging, intraoperative cancer identification, fluorescence-guided surgery, fluorescence endoscopy, fluorescence laparoscopy, robotic surgery, open field surgery, laser guided surgery, photodynamic therapy, fluorescence lifetime imaging, or a photoacoustic or sonofluorescence method.

Moreover the invention relates to a manufacturing process for the preparation of the provided dyes, the corresponding conjugates and/or the pharmaceutically acceptable salts thereof, and to their use in the preparation of a diagnostic agent.

According to a further aspect, the invention relates to a pharmaceutically acceptable composition comprising at least one dye or dye-conjugate compound of the invention, or a pharmaceutically acceptable salt thereof, in a mixture with one or more physiologically acceptable carriers or excipients. Said compositions are useful in particular as optical imaging agents to provide useful imaging of human or animal organs or tissues.

In another aspect, the present invention refers to a method for the optical imaging of a body organ, tissue or region by use of an optical imaging technique that comprises the use of an effective dose of a compound of the invention.

DETAILED DESCRIPTION OF THE INVENTION

Accordingly, it is a first object of the present invention the provision of a compound of formula (I),

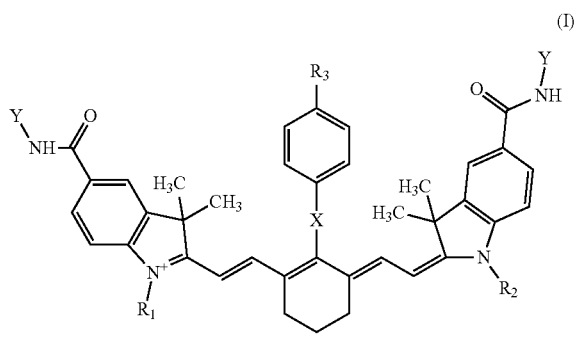

(I)

wherein
X is direct bond or —O—;
Y is a group selected from linear or branched $C_1$-$C_6$ alkyl, $C_3$-$C_7$ cycloalkyl and heterocyclyl, substituted by at least two hydroxyl groups;
R1 and R2 are each independently a linear or branched $C_1$-$C_6$ alkyl substituted by a group selected from —$SO_3H$, —COOH, —$CONH_2$ and —COO—$C_1$-$C_6$ alkyl; and
R3 is hydrogen, —$SO_3H$ or a linear or branched $C_1$-$C_6$ alkyl substituted by —COOH or —CONH—Y, wherein Y is a group selected from linear or branched $C_1$-$C_6$ alkyl, $C_3$-$C_7$ cycloalkyl and heterocyclyl, substituted by at least two hydroxyl groups,
or a stereoisomer or pharmaceutically acceptable salt thereof.

Another object of the present invention relates to the corresponding conjugated dyes represented by a compound of formula (II)

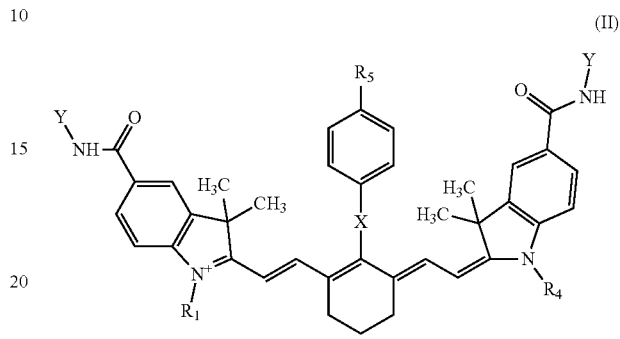

(II)

wherein
X is direct bond or —O—;
Y is a group selected from linear or branched $C_1$-$C_6$ alkyl, $C_3$-$C_7$ cycloalkyl and heterocyclyl, substituted by at least two hydroxyl groups;
R1 is linear or branched $C_1$-$C_6$ alkyl substituted by a group selected from —$SO_3H$, —COOH, —$CONH_2$ and —COO—$C_1$-$C_6$ alkyl;
R4 is linear or branched $C_1$-$C_6$ alkyl substituted by a group selected from —$SO_3H$, —COOH and —CONH—$(S)_m$-T, wherein
S is a spacer;
T is a targeting moiety; and
m is an integer equal to 0 or 1; and
R5 is selected from hydrogen, —$SO_3H$, a linear or branched $C_1$-$C_6$ alkyl, substituted by —COOH or —CONH—Y, and a group CONH—$(S)_m$-T, wherein Y, S, T and m are defined above;
and wherein at least one between R4 and R5 is linear or branched $C_1$-$C_6$ alkyl substituted by CONH—$(S)_m$-T,
or a stereoisomer or pharmaceutically acceptable salt thereof.

The present invention also relates to methods for preparing the compounds of formula (I) or (II) by means of synthetic transformations steps.

The invention also comprises compounds of formula (I) or (II) for use as fluorescent probes for biomedical optical imaging applications.

Definitions

In the present description, and unless otherwise provided, the following terms and phrases as used herein are intended to have the following meanings.

The expression "straight or branched $C_1$-$C_6$ alkyl" refers to an aliphatic hydrocarbon radical group, which may be a straight or branched-chain, having from 1 to 6 carbon atoms in the chain. For instance, "$C_4$alkyl" comprises within its meaning a linear or branched chain comprising 4 carbon atoms. Similarly, "$C_1$-$C_{20}$ alkyl" is an alkyl comprising from 1 to 20 carbon atoms. Representative and preferred alkyl groups include methyl, ethyl, n-propyl, iso-propyl, n-butyl, tert-butyl, pentyl and hexyl. Unless otherwise specified, the straight or branched $C_1$-$C_6$ alkyl is a monovalent radical group. In some cases it may be a "bivalent" or "multivalent" radical group, wherein two or more hydrogen atoms are removed from the above hydrocarbon radical group and substituted, e.g. methylene, ethylene, iso-propylene groups and the like.

The term "$C_3$-$C_7$ cycloalkyl" as used therein comprises within its meaning a saturated (i.e. cycloaliphatic) carbocyclic ring comprising from 3 to 7 carbon atoms. Suitable examples include a $C_5$-$C_7$ carbocyclic ring, e.g. a cyclohexyl ring.

The term "heterocyclyl" as used therein comprises a saturated cycloaliphatic ring, preferably a 5-7 membered saturated ring, further comprising an heteroatom in the cyclic chain selected from N, O and S. Preferably, it refers to tetrahydropyran.

The term "hydroxyalkyl" refers to any of the corresponding alkyl chain wherein one or more hydrogen atoms are replaced by hydroxyl groups.

The term "alkoxy" comprises within its meaning an alkyl chain as above defined further comprising one or more oxygen atoms; examples include, for instance, alkyl-oxy groups such as methoxy, ethoxy, n-propoxy, iso-propoxy and the like, and alkyl-(poly)oxy groups in which the alkyl chain is interrupted by one or more oxygen atoms.

In the present description the term "protecting group" (Pg) designates a protective group adapted for preserving the function of the group to which it is bound. Specifically, protective groups are used to preserve amino, hydroxyl or carboxyl functions. Appropriate protective groups may include, for example, benzyl, carbonyl, such as formyl, 9-fluoromethyloxycarbonyl (Fmoc), benzyloxycarbonyl (Cbz), t-butoxycarbonyl (Boc), isopropyloxycarbonyl or allyloxycarbonyl (Alloc), alkyl, e.g. tert-butyl or triphenylmethyl, sulfonyl, acetyl groups, such as trifluoroacetyl, benzyl esters, allyl, or other substituents commonly used for protection of such functions, which are well known to the person skilled in the art (see, for instance, the general reference T. W. Green and P. G. M. Wuts, Protective Groups in Organic Synthesis, Wiley, N.Y. 2007, $4^{th}$ Ed., Ch. 5).

Moreover, the invention comprises also the precursors or intermediates compounds suitable for the preparation of a desired compound of formula (I) or salts thereof. In such derivatives the functional groups of R1-R5, such as a carboxylic acid or carboxamide, can be protected with an appropriate protecting group (Pg) as defined above, preferably with alkyl or ester groups. If necessary, also hydroxyl groups of Y groups can be protected with an appropriate protecting group (Pg) during the preparation of the compounds of formula (I) or (II), thus forming for instance acetoxy, alkoxy or ester groups.

The expression "coupling reagent" refers to a reagent used for instance in the formation of an amide bond between a carboxyl moiety and an amino moiety. The reaction may consist of two consecutive steps: activation of the carboxyl moiety and then acylation of the amino group with the activated carboxylic acid. Non limiting examples of such coupling agents are selected from the group consisting of: carbodiimides, such as N,N'-diisopropylcarbodiimide (DIC), N,N'-dicyclohexylcarbodiimide (DCC), 1-ethyl-3-(3-dimethylaminopropyl) carbodiimide (EDAC), 1-ethyl-3-(3-dimethylaminopropyl)carbodiimide (EDC) and 1-ethyl-3-(3-dimethylaminopropyl)carbodiimide (WSC); phosphonium reagents, such as (benzotriazol-1-yloxy)tris (dimethylamino)phosphonium hexafluorophosphate (BOP), (benzotriazol-1-yloxy)tripyrrolidinophosphonium hexafluorophosphate (PyBOP), 7-azabenzotriazol-1-yloxy-tripyrrolidino-phosphonium hexafluorophosphate (PyAOP), [ethyl cyano(hydroxyimino)acetato-O2]tri-1-pyrrolidinylphosphonium hexafluorophosphate (PyOxim), bromotripyrrolidinophosphonium hexafluorophosphate (PyBrOP) and 3-(diethoxyphosphoryloxy)-1,2,3-benzotriazin-4(3H)-one (DEPBT); and aminium/uronium-imonium reagents, such as N,N,N',N'-tetramethyl-O-(benzotriazol-1-yl)uronium tetrafluoroborate (TBTU), N,N,N',N'-tetramethyl-O-(1H-benzotriazol-1-yl)uronium hexafluorophosphate (HBTU), N,N,N',N'-tetramethyl-O-(7-azabenzotriazol-1-yl)uronium hexafluorophosphate (HATU), O-(1H-6-chlorobenzotriazole-1-yl)-1,1,3,3-tetramethyluronium hexafluorophosphate (HCTU), 1-[1-(cyano-2-ethoxy-2-oxoethylidene-aminooxy)-dimethylamino-morpholino]-uronium hexafluorophosphate (COM U) and fluoro-N,N,N',N'-tetramethylformamidinium hexafluorophosphate (TFFH) or other compounds well known to the person skilled in the art.

The terms "small molecule" is broadly used therein to refer to an organic, inorganic or organometallic compound having a molecular weight of less than about 5000 Daltons and being able to regulating a biological process or causing a biological effect when administered to an animal, including humans. The term "small molecule" can be also used interchangeably with the terms "drug" or "biologically active moiety". For instance, it can include any agent, active molecule or compound which provides a beneficial effect against tumors and produces a localized or systemic effect in a patient by binding a specific biological target. A small molecule can also refer to a portion or residue of a parent drug, which is activated or chemically modified from thereof and covalently attached to a conjugated dye of the invention.

The expression "activated carboxylic acid" refers to a derivative of a carboxyl group that is more susceptible to nucleophilic attack than a free carboxyl group; suitable derivatives may include for instance acid anhydrides, thioesters, acyl halides, NHS ester and sulfo NHS esters.

Moreover, the terms "moiety" or "residue" are herewith intended to define the residual portion of a given molecule once properly attached or conjugated, either directly or through a suitable linker and/or spacer, to the rest of the molecule.

Targeting Moiety (T)

According to the invention, a targeting moiety (T) is a molecule that binds with particular selectivity to a biological target and facilitates the accumulation of the contrast agent in a specific tissue or part of the body. Generally, it is represented by a natural or synthetic molecule for use in biological systems.

Such specific binding can be achieved through a ligand, such as for instance a small molecule, a protein, a peptide, a peptidomimetic, an enzyme substrate, an antibody or fragment thereof or an aptamer, interacting with a specific biological target expressed on the surface of the tissues or cells of interest.

Suitable biological targets for the compounds of the invention can be for instance an epithelial growth factor (EGF) receptor, such as EGFR or HER2; a vascular endothelial growth factor (VEGF) receptor, such as VEGFR1 or VEGFR2; a carbonic anhydrase (CA) enzyme, such as CAIX, CAII or CAXII; a mucin glycoprotein, such as MUC1; a glucose transporter, such as GLUT-1; a sodium-hydrogen antiporter, such as NHE1; a carcinoembryonic glycoprotein, such as the carcinoembryonic antigen (CEA); a chemokine receptor, such as the chemokine receptor type 4 (CXCR4); a cell adhesion molecule, such as ICAM, EPCAM, VCAM, E-Selectin, P-Selectin; the hepatocyte growth factor HGFR (c-met); a receptor for the transferrin; a ephrin receptor, such as EPHA2; a receptor for the folic acid, such as FR-alpha; a glycoprotein binding ialuronic acid, such as CD44; a bombesin receptor, such as BB1, BB2, BB3; a N-acetyl-L-aspartyl-L-glutamate (NAAG) peptidase, such as prostate-specific membrane antigen (PSMA); and, in particular, an integrin receptor, such as $\alpha_v\beta_3$, $\alpha_v\beta_5$, $\alpha_v\beta_6$ or $\alpha_5\beta_1$ integrin receptors.

For instance, integrin receptors targeting moieties are represented by linear or cyclic peptides comprising the sequence Arg-Gly-Asp (RGD). This tripeptide has high binding specificity for the receptor, being recognized as ligand by the family of the integrin receptors located in the cell membrane. In fact, it has been identified in some extracellular matrix glycoproteins, such as fibronectin or vitronectin, which exploit this RGD motif to mediate cell adhesion.

Therefore, linear and cyclic peptides and peptidomimetics containing the sequence Arg-Gly-Asp (RGD), such as for instance cRGD, cRGDfK, cRGDyK, cRGDfC, RGD-4C, RGD-2C, AH111585, NC100692, RGD-K5 (Kapp et al., Sci Rep, 2017, 7: 3905), or their analogues and derivatives thereof, are a well known example of binding motif targeting cancer tissues on which cell membrane integrins are up-regulated compared to healthy tissues.

In one embodiment, the compounds of the invention can be conjugated to vectors known to target the prostate-specific membrane antigen (PSMA), thus allowing the detection and imaging of prostate cancer. These ligands are represented for instance by the vector glutamic acid-urea-lysine (EuK) or other PSMA binding vectors of formula "EuX" as described in EP3636635 A1, namely glutamic acid linked to another amino acid or similar via a bridging urea, for example EuFA (glutamic acid-urea-3-(2-furyl)-alanine), EuPG (glutamic acid-urea-2-(2'-propynyl)-alanine), EuE (glutamic acid-urea-glutamic acid), or other urea-based peptidomimetics, such as for instance EuK-(3-(2-naphtyl)-alanine)-tranexamic acid, as described in Benešová et al., J Nucl Med 2015, 56: 914-920.

In another embodiment, the compounds of the invention can be conjugated to other small molecules, peptides, proteins or antibodies, such as for instance monoclonal antibodies already used for therapy. Small molecules containing the drug acetazolamide, such as for instance compounds 4a, 5a, 6a, 7a and 8a (Wichert et al., Nat Chem 2015, 7: 241-249), or their analogues and derivatives thereof, are examples of small molecules targeting the enzyme CAIX. Linear and cyclic peptides and peptidomimetics, such as peptide GE11 (described in Li et al., FASEB J 2005, 19: 1978-85) and/or peptide L1 (described in Williams et al., Chem Biol Drug Des 2018, 91:605-619), or their analogues and derivatives thereof, are examples of peptides targeting the epithelial growth factor receptor (EGFR). Among the proteins, derivatives of the epithelial growth factor (EGF) are examples of small protein targeting the epithelial growth factor receptor (EGFR). Among the antibodies, panitumumab and cetuximab are examples of monoclonal antibodies targeting the epithelial growth factor receptor (EGFR).

Preferably, the targeting ligands of the invention are able to selectively link tumor cells or tissues. In particular they are able to link tumors selected from brain cancer, breast cancer, head and neck cancer, ovarian cancer, prostate cancer, esophageal cancer, skin cancer, gastric cancer, pancreatic cancer, bladder cancer, oral cancer, lung cancer, renal cancer, uterine cancer, thyroid cancer, liver cancer, and colorectal cancer. In addition, the targeting ligands are able to link metastatic spreads of the above-mentioned cancers in tissues and organs different from the primary source. Furthermore, the targeting ligands are able to link pre-neoplastic lesions and dysplasia in different tissues and organs.

Spacer S

According to the invention, S is a spacer, optionally present, that separates the targeting moiety from the dye. The presence of a spacer is particularly relevant for some embodiments where the targeting moiety and the dye risk to adversely interact with each other. Moreover, the presence of the spacer may be necessary when the dye is relatively large and may interfere with the binding of the targeting moiety to the target site.

The spacer can be either flexible (e.g., simple alkyl chains) or rigid (e.g., cycloalkyl or aryl chains) so that the dye is oriented away from the target. The spacer can also modify pharmacokinetic and metabolism of the conjugates of formula (I) used as imaging agents in a living organism.

Hydrophilic spacers may reduce the interaction with plasma proteins, reduce blood circulation time and facilitate excretion. For example, if the spacer is a polyethyleneglycol (PEG) moiety, the pharmacokinetics and blood clearance rates of the imaging agent in vivo may be altered. In such embodiments, the spacer can improve the clearance of the imaging agent from background tissue (i.e., muscle, blood) thus giving a better diagnostic image due to high target-to-background contrast. Moreover, the introduction of a particular hydrophilic spacer may shift the elimination of the contrast agent from hepatic to renal, thus reducing overall body retention.

Therefore, in one preferred embodiment, the spacer is an hydrophilic moiety comprising $C_1$-$C_{20}$ alkyl, $C_3$-$C_7$ cycloalkyl or aryl groups. Preferably, the spacer is selected from the group consisting of $-(CH_2)_pCOO-$, $-(CH_2CH_2O)_pCH_2CH_2COO-$ and $-(CH_2CH_2O)_pCH_2CH_2NH-$, wherein p is an integer between 0 and 20. Preferably p is 2, 6 or 12.

When not necessary, the spacer is preferably absent, i.e. m is 0 and S represents a direct bond. The spacer, or alternatively the targeting moiety when the spacer is absent, can be connected in a compound of formula (II), alternatively at the R4 and/or R5 residue.

The linking groups of R4-R5 are reactive functional groups such as carboxylic acid or carboxamido residues suitable for conjugating the dye to the targeting moiety by formation of a chemical bond.

For instance, when an amine-containing targeting moiety (T) is conjugated with a compound of formula (II) wherein R4 and/or R5 is an alkyl substituted by carboxylic acid, this carboxylic acid may be optionally activated before carrying out the conjugation through conversion in a more reactive form using an activating reagent, forming for example a N-hydroxy succinimide (NHS) ester or a mixed anhydride. Then, to obtain the corresponding compound of formula (II), the amine-containing targeting moiety is treated with the resulting activated acid to form an amide linkage. Typically, this reaction is carried out in aqueous buffer, optional co-solvent with DMSO or DMF at pH 8 to 9, or in organic solvent with organic bases such as DIPEA, TEA or NMM.

Otherwise a direct conjugation using the "non-activated" carboxylic acid may be performed.

Similarly, when the linking group of R4 and/or R5 is a carboxamido group, the procedure for attachment of the suitable targeting moiety is analogous, but no activation step of the linker is generally required and the dye and targeting moiety are treated directly.

The compounds of the above formula (I) or (II) may have one or more asymmetric carbon atoms, otherwise referred to as chiral carbon atoms, and may thus give rise to diastereomers and optical isomers. Unless otherwise provided, the present invention further includes all such possible diastereomers as well as their racemic mixtures, their substantially pure resolved enantiomers, all possible geometric isomers, and pharmaceutically acceptable salts thereof.

As a non limiting example, when the dyes of formula (I) or (II) are substituted by a D-glucamine group (Y is $C_6$ alkyl substituted with five hydroxy groups), the invention comprises the corresponding enantiomerically pure compounds as well as any stereoisomers thereof, for instance compounds bearing a L-glucamine group or any possible mixtures of D-/L-enantiomers thereof.

The present invention further relates to compounds of the above formula (I) or (II) in which the functional groups of R1, R2/R4 and/or R3/R5, e.g. the sulfonyl, carboxyamino or carboxylic acid groups, may be in the form of a pharmaceutically acceptable salt.

In one embodiment, the invention relates to a compound of formula (I) or (II) wherein Y is selected from a linear or branched $C_1$-$C_6$ alkyl, cycloalkyl and heterocyclyl, substituted with from two to five hydroxyl groups.

In a preferred embodiment the invention relates to a compound of formula (I) or (II) wherein Y is selected from the group consisting of

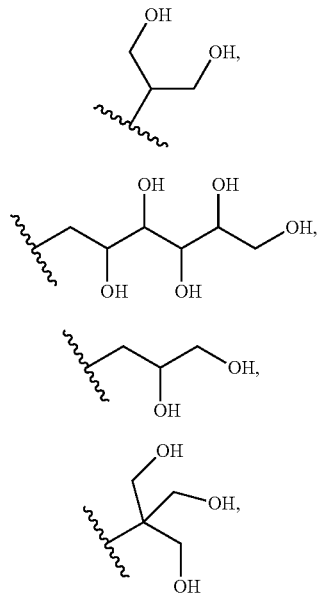

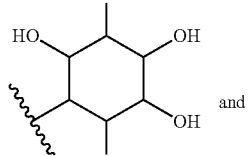

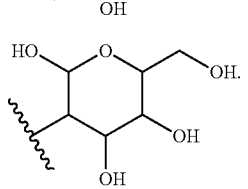

More preferably, the invention relates to a compound of formula (I) or (II) wherein Y is a group of formula (ii) as defined above. Preferably, the group (ii) has the following stereochemical configuration obtained by using a D-glucamine in the preparation of the compounds:

Another embodiment of the invention relates to a compound of formula (II) wherein m is 0 and the spacer S is represented by a direct bond or m is 1 and the spacer is an hydrophilic moiety comprising $C_1$-$C_{20}$ alkyl, $C_3$-$C_7$ cycloalkyl or aryl groups. Preferably, the spacer is selected from —$(CH_2)_p COO$—, —$(CH_2CH_2O)_p CH_2CH_2COO$— and —$(CH_2CH_2O)_p CH_2CH_2NH$—, wherein p is an integer between 0 and 20. Preferably p is 2, 6 or 12.

In a further embodiment, T is a targeting moiety selected from a small molecule, a protein, a peptide, a peptidomimetic, an enzyme substrate, an antibody or any fragment thereof and an aptamer.

Preferably T is represented by a peptide, and in particular by a moiety interacting with an integrin receptor, such as $\alpha_v\beta_3$, $\alpha_v\beta_5$, $\alpha_v\beta_6$, $\alpha_5\beta_1$ and the like, preferably with $\alpha_v\beta_3$ integrin receptor.

In a preferred embodiment, R1 is a linear $C_4$ alkyl substituted by —$SO_3H$.

In another preferred embodiment, the invention relates to a compound of formula (I) or (II) wherein Y represents a group (ii) as defined above, otherwise represented by the following formula (Ia) or (IIa) respectively:

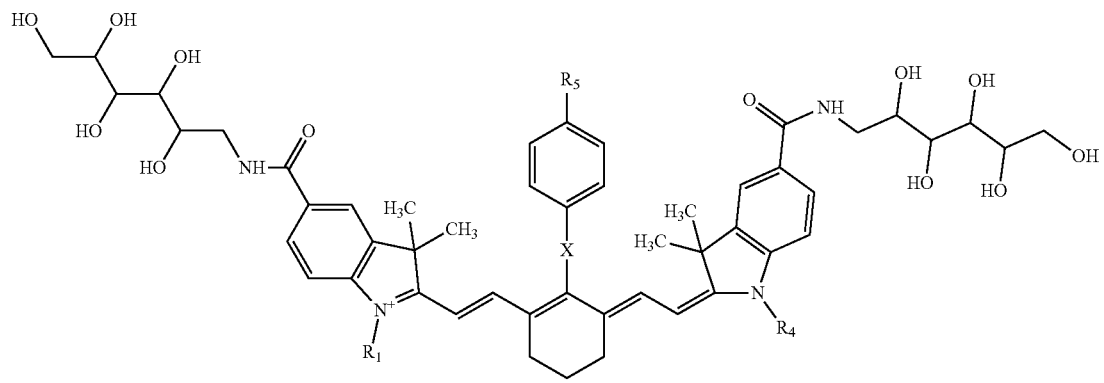
wherein R1, R2, R3, R4, R5 and X are as defined above.
Especially preferred are the compounds of formula (I) listed in Table Ia and the compounds of formula (II) listed in Table Ib.
TABLE Ia
Preferred compounds of formula (I)
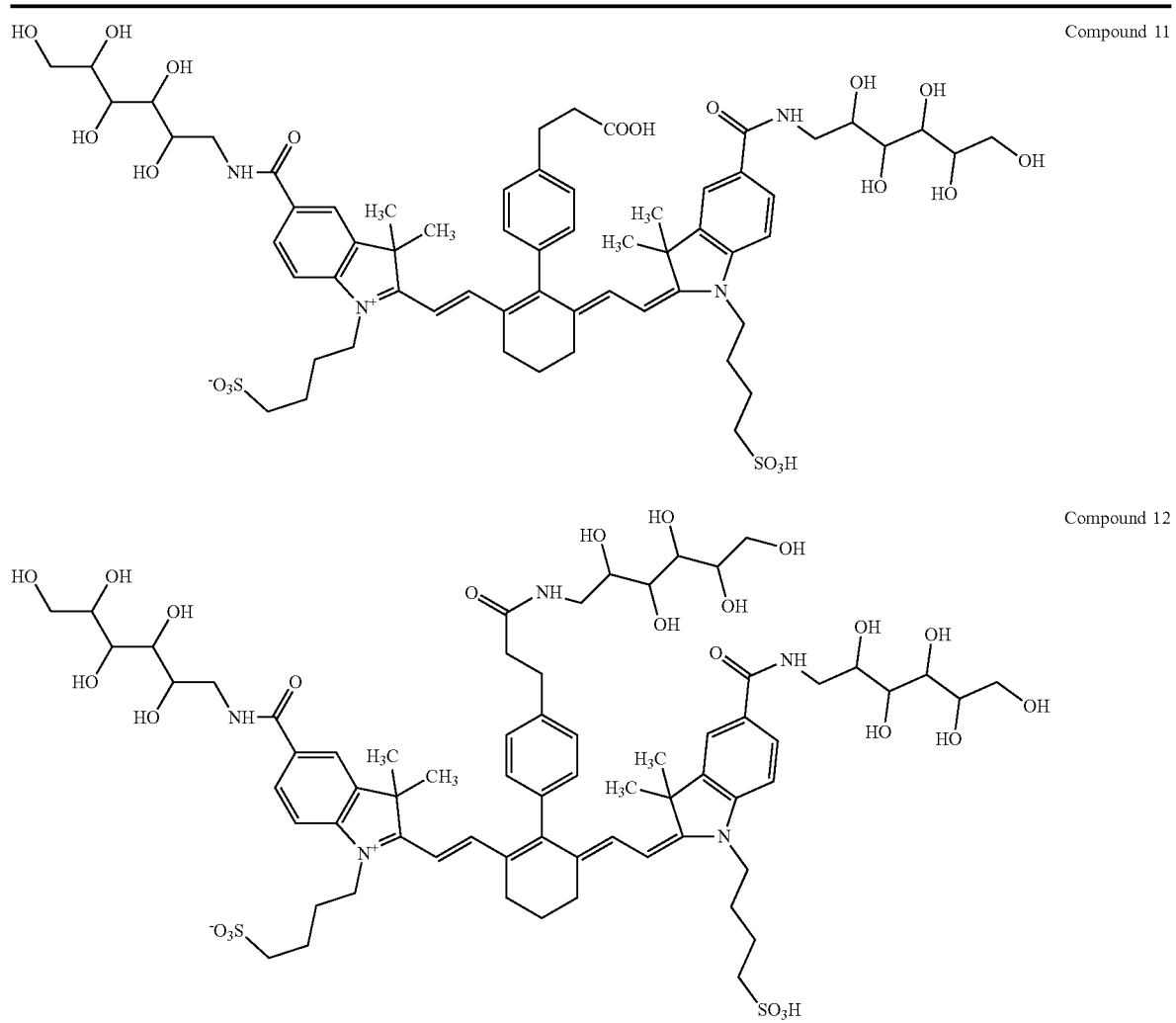

TABLE Ia-continued
Preferred compounds of formula (I)
Compound 13
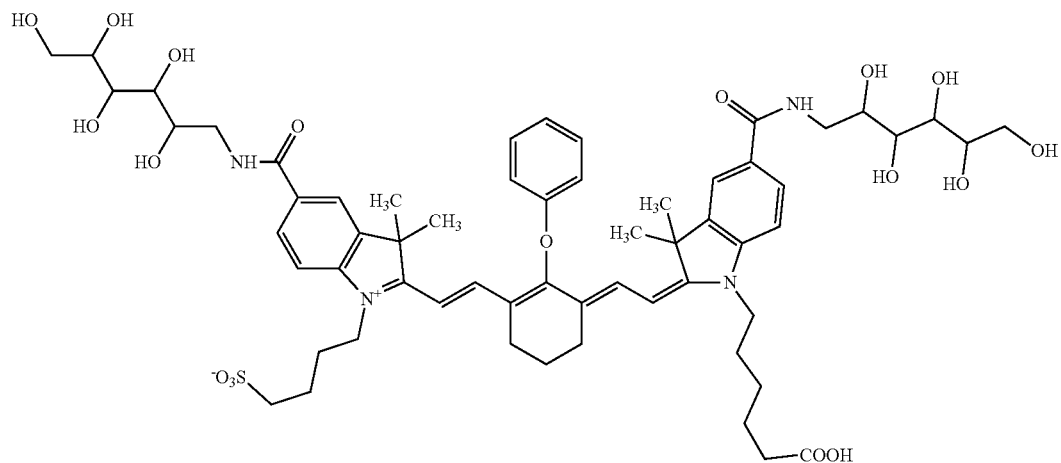
Compound 14
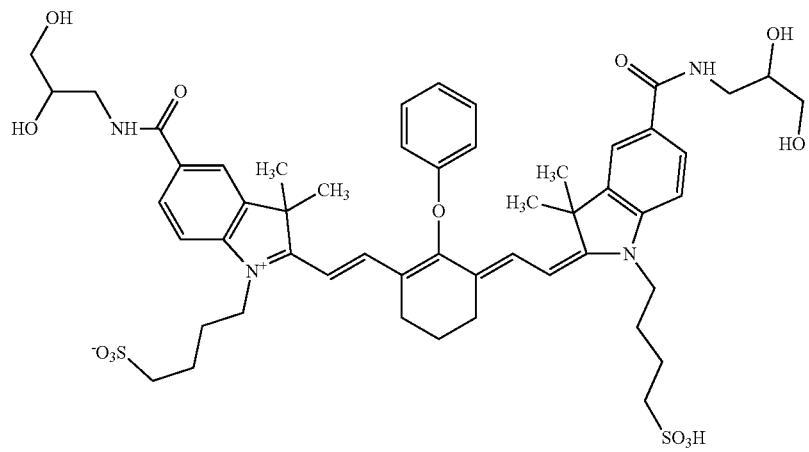
Compound 15
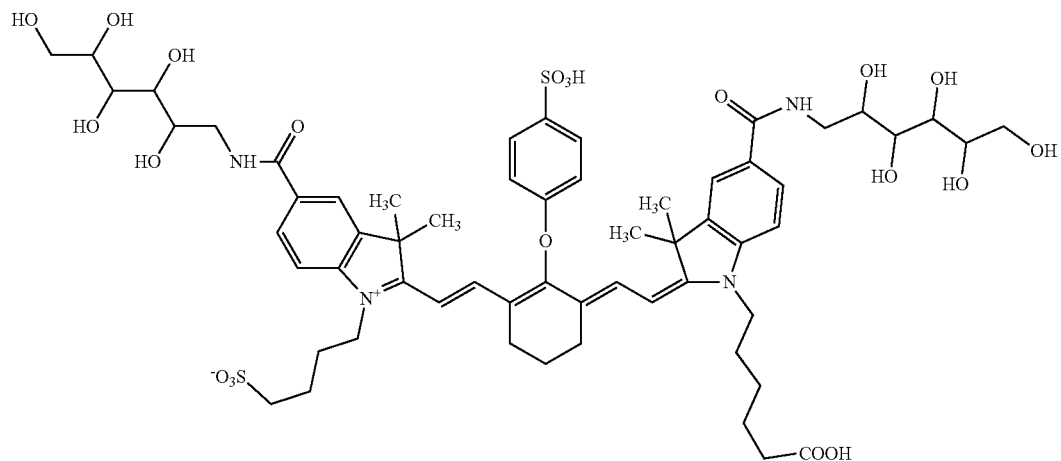

TABLE Ia-continued
Preferred compounds of formula (I)
Compound 16
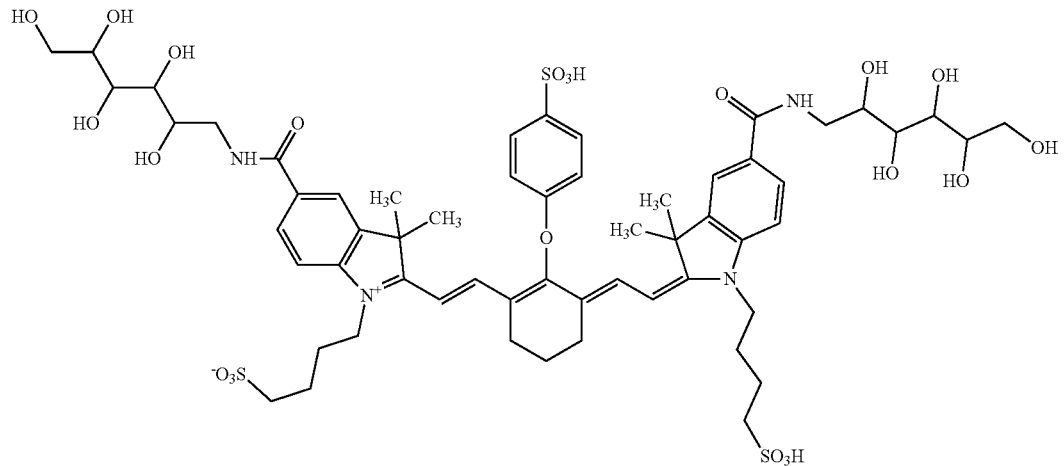
Compound 17
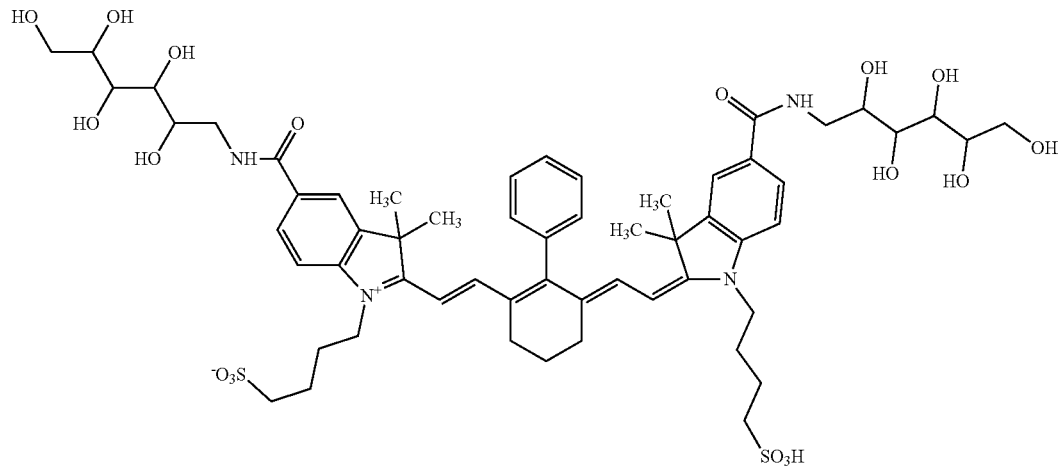
Compound 18
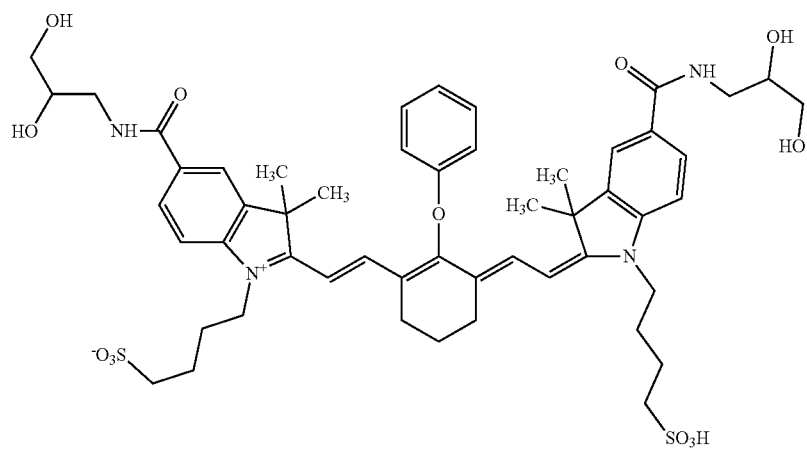

TABLE Ia-continued
Preferred compounds of formula (I)
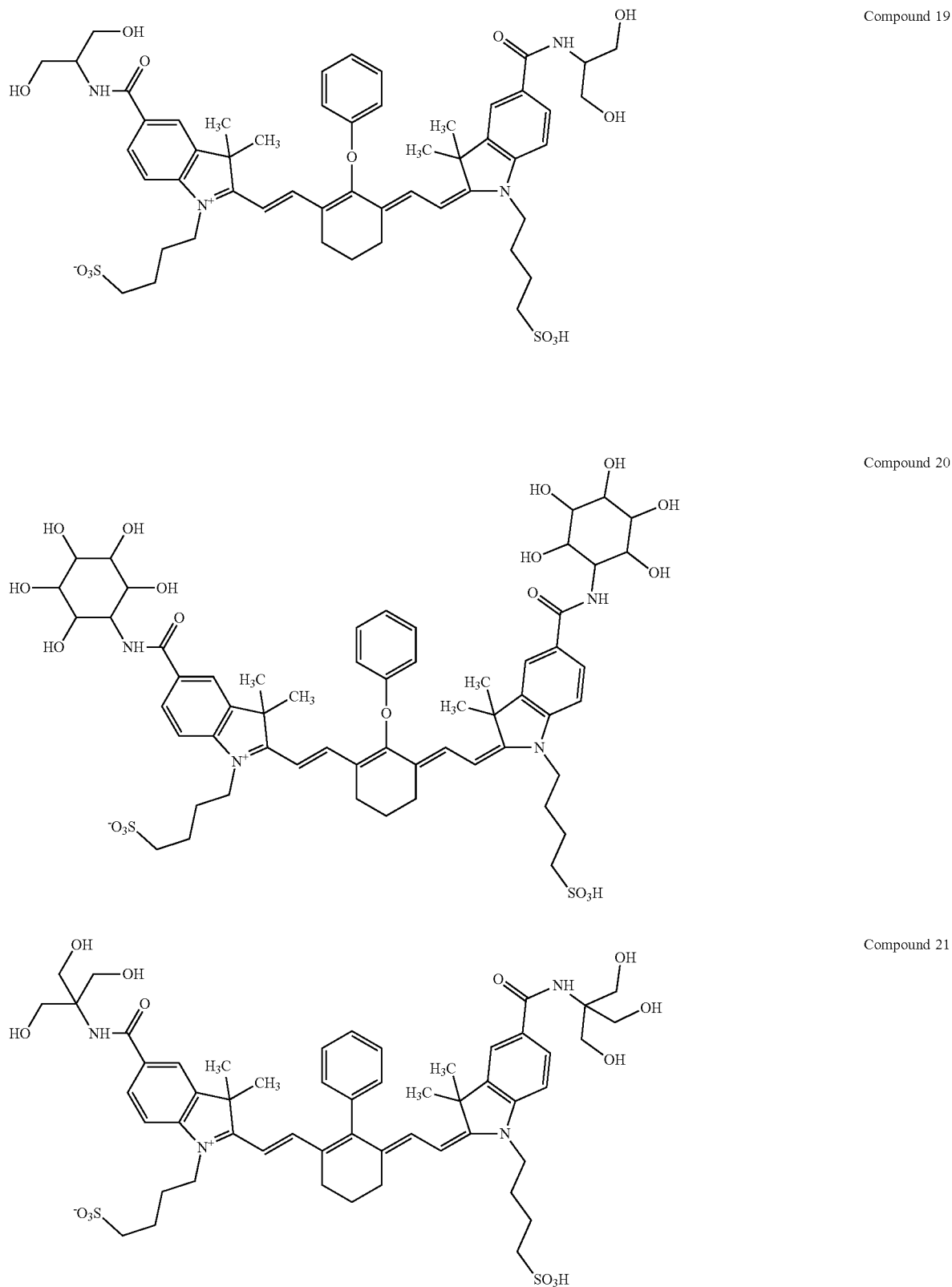
Compound 19
Compound 20
Compound 21

TABLE Ia-continued
Preferred compounds of formula (I)
Compound 22
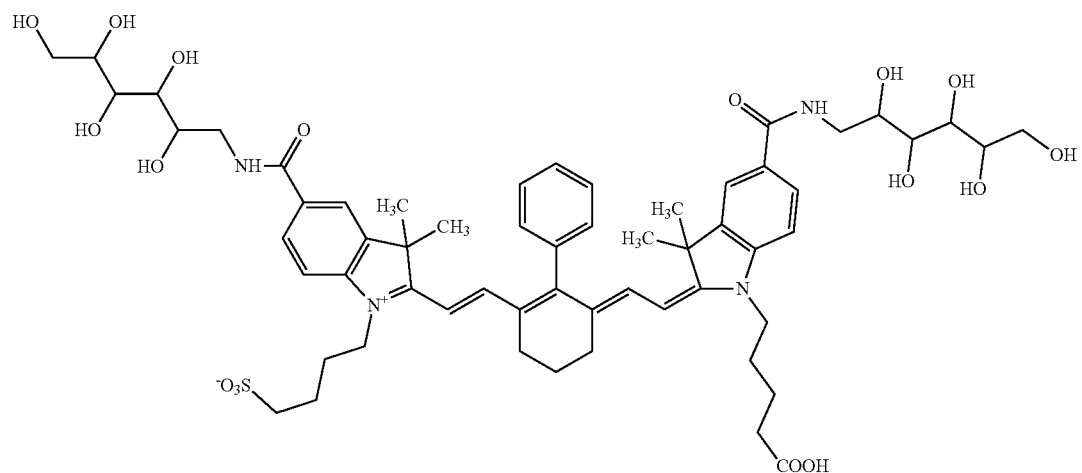
Compound 23
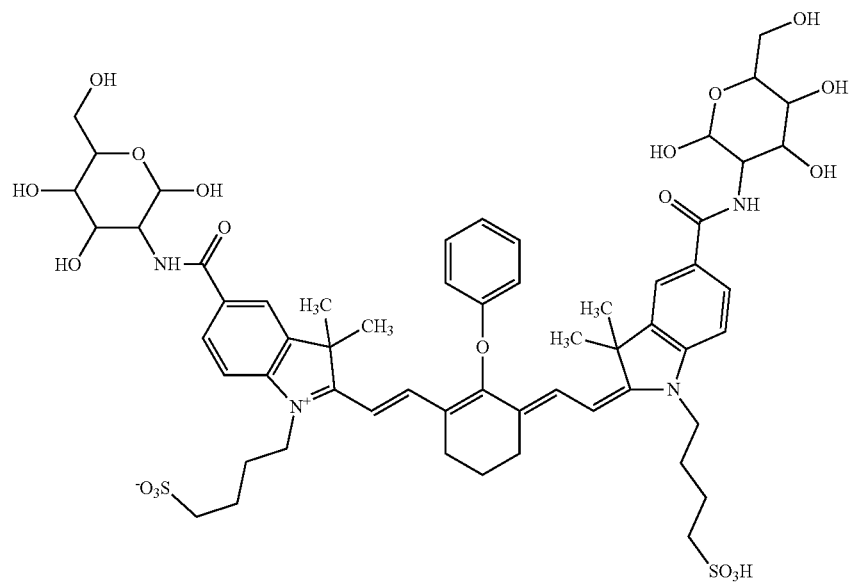

TABLE Ib
Preferred conjugated dyes of formula (II)
Compound 1
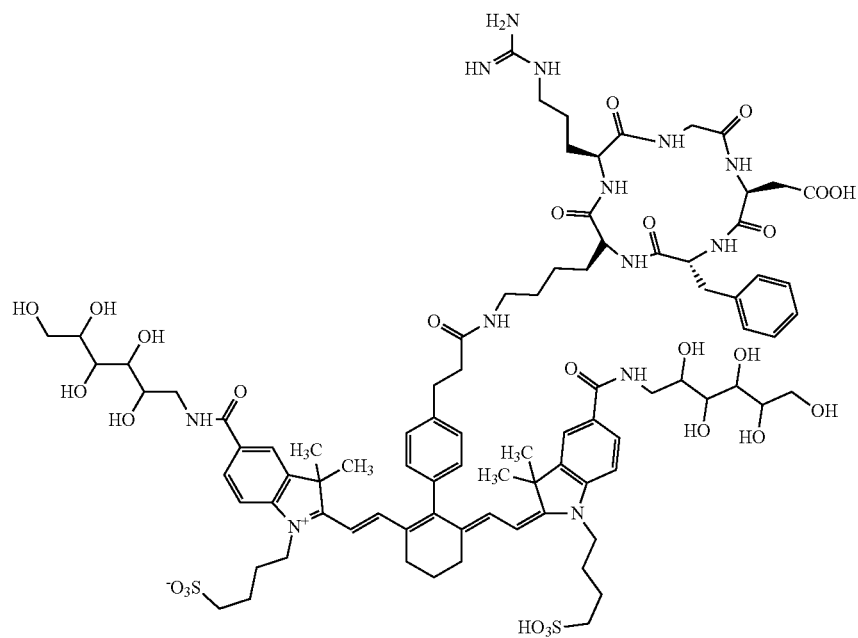
Compound 2
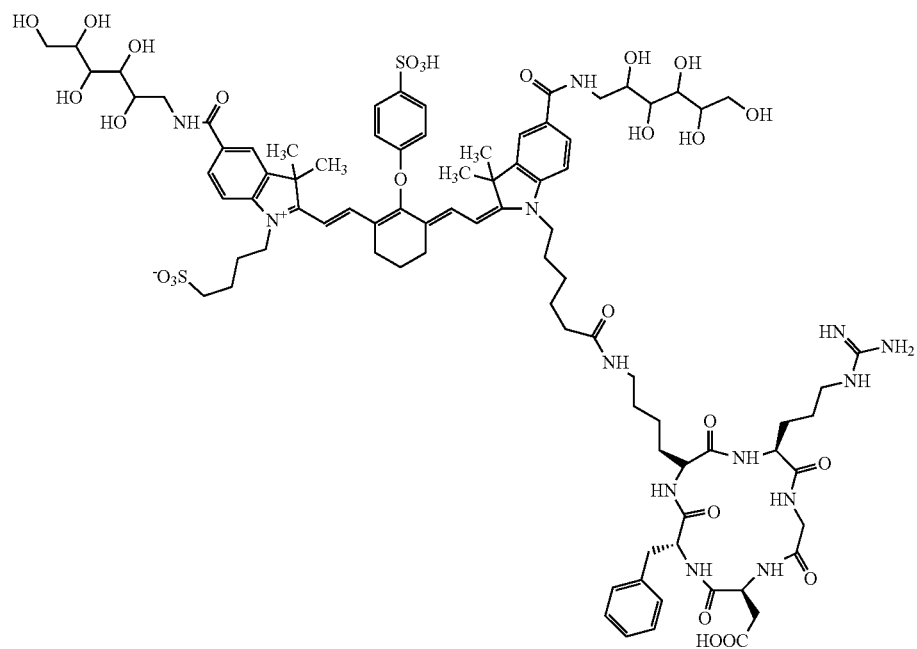

TABLE Ib-continued
Preferred conjugated dyes of formula (II)
Compound 3
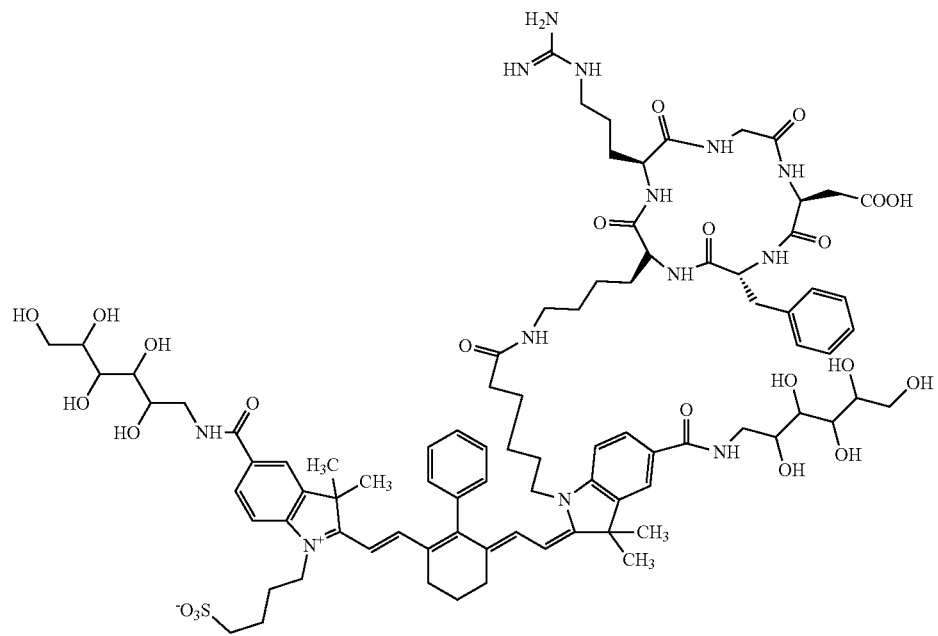
Compound 4
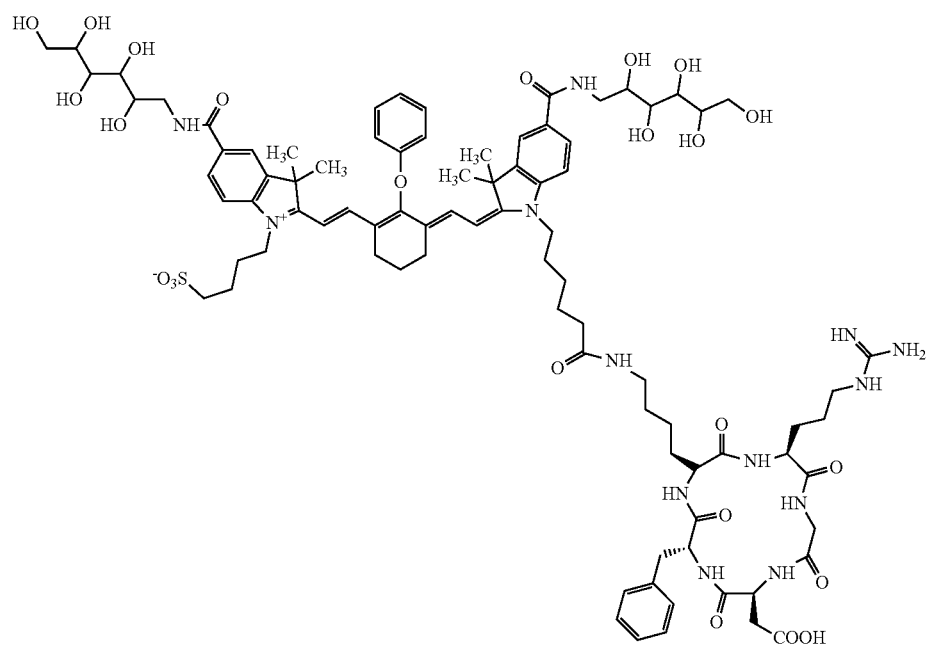

TABLE Ib-continued
Preferred conjugated dyes of formula (II)
Compound 5
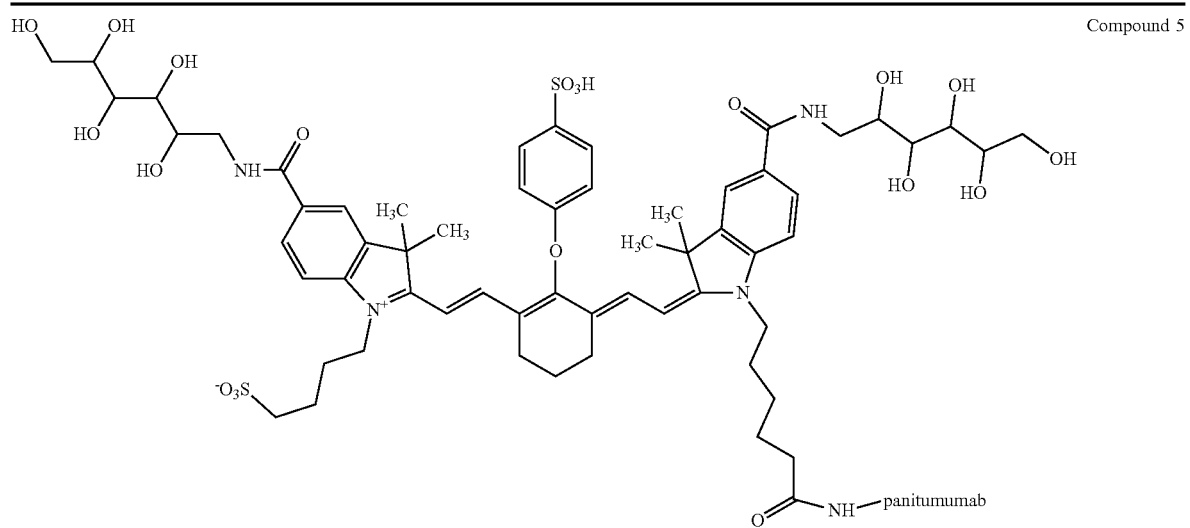
Compound 6
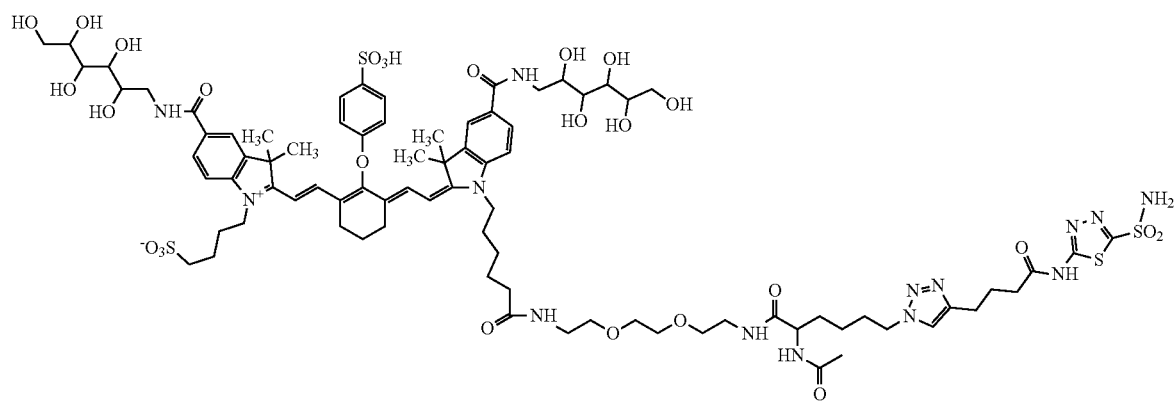
Compound 7
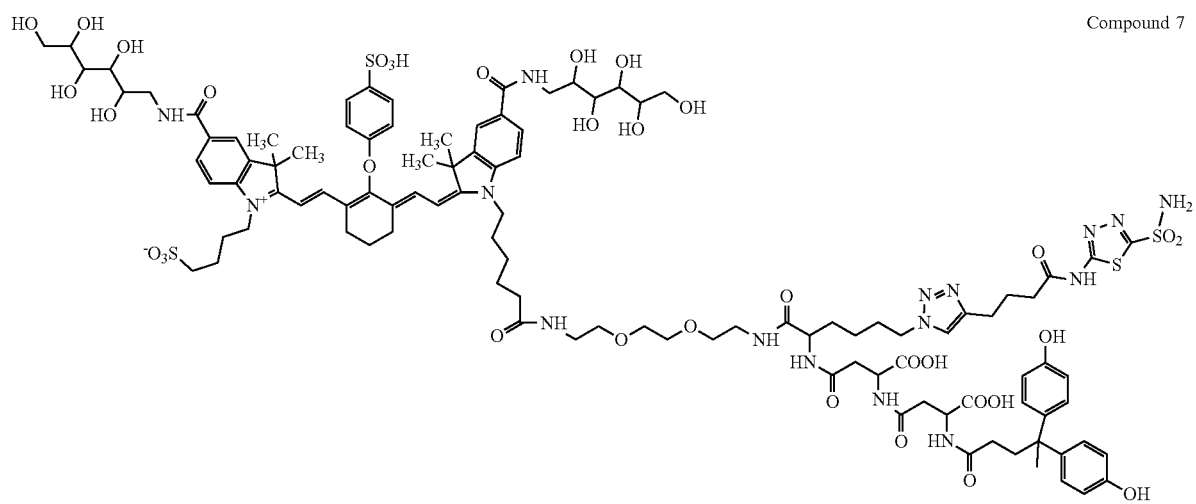

TABLE Ib-continued

Preferred conjugated dyes of formula (II)

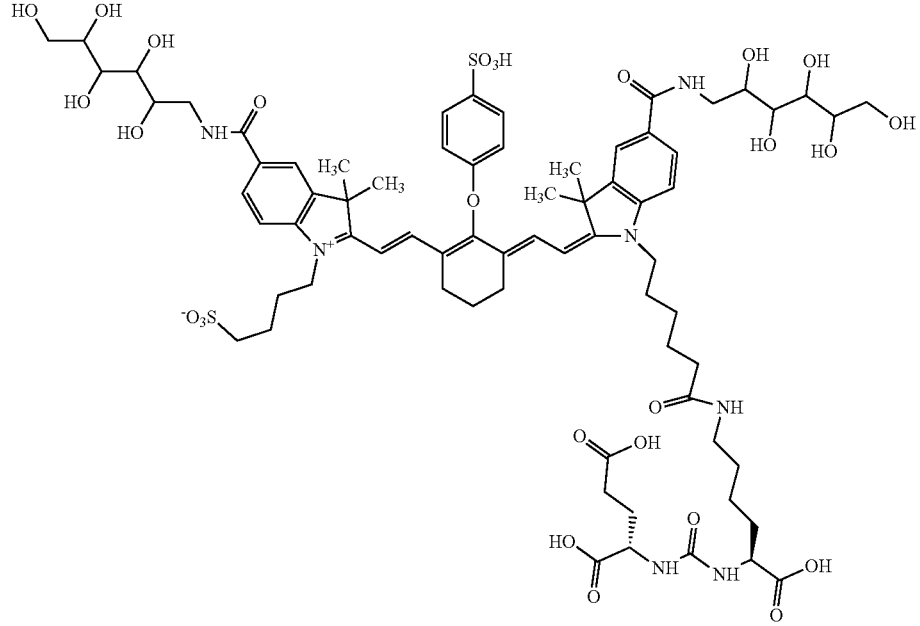

Compound 8

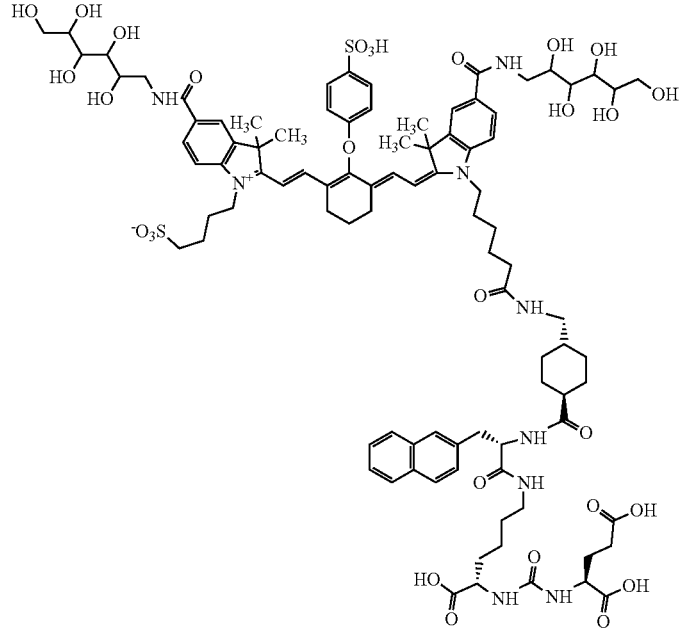

Compound 9

The present invention is also directed to methods for synthesizing the compounds of formula (I) or (II), prepared as illustrated in the following of the description, which are near-infrared dyes optionally conjugated to a targeting moiety through a linking group.

Accordingly, the invention provides the compounds of formula (I) or (II) as defined above for use as optical imaging agents for diagnostic biomedical applications in mammals (humans and animals). Preferably the imaged mammal subject is a human.

In a preferred embodiment, the compounds of the invention are for use as imaging agents in the detection of normal (healthy) tissues or abnormal (pathologic) tissues, in particular a tumor.

Preferably, the compounds of formula (I) or (II) as defined above are for use in the detection of normal (healthy) tissues by means of imaging techniques comprising for instance angiography, perfusion imaging, bile duct imaging and nerve imaging.

In a further preferred embodiment, the invention provides for compounds of formula (I) or (II) as defined above for use in the detection of abnormal (pathologic) tissue such as for instance a primary tumor lesion, local or distant metastases, or a pre-neoplastic lesion, in particular dysplasia and hyperplasia. In particular, the compounds of formula (II) as defined above are preferably for use in the detection and demarcation of a tumor margin in guided surgery of an individual patient. A preferred use is wherein said tumor is a tumor showing a over-expression of a biological epitope, for instance selected from a receptor, an enzyme, a glycoprotein, a lipid raft, a transmembrane protein located on the cell surface and a soluble factor present in serum, plasma or the interstitial space. Preferably, said biological epitope is an integrin receptor for Vitronectin, Fibrogen and/or for the transforming growth factor-β (TGF-β).

The invention also provides a compound of formula (I) or (II) for use as fluorescent probe as defined above, wherein the detection and demarcation of the tumor is carried out under NIR radiation. Preferably, such detection and demarcation of tumor is carried out before, during or after a surgical procedure to remove such tumor tissue. A fluorescence-guided surgery procedure is an example of such use.

Additionally, the invention provides compounds of formula (I) or (II) as defined above for use in the detection of an inflamed tissue, a fibrotic tissue, an ischemic tissue, or a tissue with abnormal metabolic rate.

The invention also provides for a method of imaging tissues and cells comprising the steps of:
i) contacting the cells or tissues with a compound of formula (I) and (II);
ii) irradiating the tissues or cells at a wavelength absorbed by the imaging agent;
iii) detecting the near-infrared emission using a fluorescence camera.

Preferably, said contacting the cells or tissues with the imaging agents of formula (I) or (II) is accomplished by topical or local application (e.g., by spraying, soaking or applying an ointment, foam or cream) or by systemic application (enteral or parenteral administration).

The invention further relates to a pharmaceutical diagnostic composition comprising a compound of formula (I) or a conjugate of formula (II) as defined above, and at least one pharmaceutically acceptable carrier or excipient.

In particular, the invention relates to a pharmaceutical composition comprising a dye of formula (I), or a salt thereof, and one or more pharmaceutically acceptable adjuvants, excipients or diluents. Alternatively, the invention relates to a pharmaceutical composition comprising a conjugate of formula (II) wherein R4 and/or R5 is $C_1$-$C_6$ alkyl substituted with CONH—$(S)_m$-T as defined above, or a salt thereof, and one or more pharmaceutically acceptable adjuvants, excipients or diluents.

Another aspect of this invention relates to a diagnostic kit comprising a compound of formula (I) or (II) as defined above. In addition, the kit can contain additional adjuvants for implementing the optical imaging. These adjuvants are, for example, suitable buffers, vessels, detection reagents or directions for use. The kit preferably contains all materials for an intravenous administration of the compounds of the invention.

The compounds of the invention may be administered either systemically or locally to the organ or tissue to be imaged, prior to the imaging procedure. For instance, the compounds can be administered intravenously. In another embodiment they may be administered parenterally or enterally.

The compositions are administered in doses effective to achieve the desired optical image of a tumor, tissue or organ, which can vary widely, depending on the compound used, the tissue subjected to the imaging procedure, the imaging equipment being used and the like.

The exact concentration of the imaging agents is dependent upon the experimental conditions and the desired results, but typically may range between 0.000001 mM to 0.1 mM. The optimal concentration is determined by systematic variation until satisfactory results with minimal background fluorescence are obtained.

Once administered, the imaging agents of the invention are exposed to a light, or other form of energy, which can pass through a tissue layer. Preferably the radiation wavelength or waveband matches the excitation wavelength or waveband of the photosensitizing agent and has low absorption by the non-target cells and the rest of the subject, including blood proteins.

Typically, the optical signal is detectable either by observation or instrumentally and its response is related to the fluorescence or light intensity, distribution and lifetime.

Description of the Syntheses

The preparation of the compounds of formula (I) or (II), as such or in the form of physiologically acceptable salts, represents a further object of the invention. The cyanine dyes and dye-conjugates of the invention can be prepared for instance according to the methods described in the following sections and in the experimental part.

A general teaching about the preparation of cyanine dyes can be found in Mujumdar R. B. et al., Bioconjugate Chem. 1993, 4(2): 105-111, which relates to the synthesis and labeling of sulfoindocyanine dyes. However, the cyanines of the present invention are characterized by a specific functionalization pattern not present in the compounds of the art, for which the set up of a proper synthetic approach was required. In fact, unlikely other known cyanines, the compounds of the invention bears even three functional moieties (carboxylic acid or amido groups) to be derivatized in different ways, so that the use of protecting groups is necessary in most cases to direct the reactions on the desired functional group.

It is known that difficulties can arise when manipulating the cyanines at the strong pH and temperature conditions necessary for the removal of the protecting groups, since the stability of the cyclohexenyl-polymethine scaffold can be compromised in some cases, with severe degradation of the dyes.

Moreover, further obstacles can be encountered due to a possible hydrolysis and degradation of the amide groups —CONH—Y when deprotecting a carboxylic group of R1-R5 (typically, amide derivatives can hydrolyze in concentrated alkaline medium, see for instance Yamana et al, *Chem. Pharm. Bull.*, 1972, 20(5), 881-891).

In one preferred embodiment, the protective group for the moiety R4 or R5 is an ester group. More preferably, an ethyl ester group can be advantageously used.

Preparation of Cyanine Dyes of Formula (I)

According to the invention, compounds of formula (I) can be prepared through the general sequence of synthetic steps as reported in the following Scheme 1.

Scheme 1
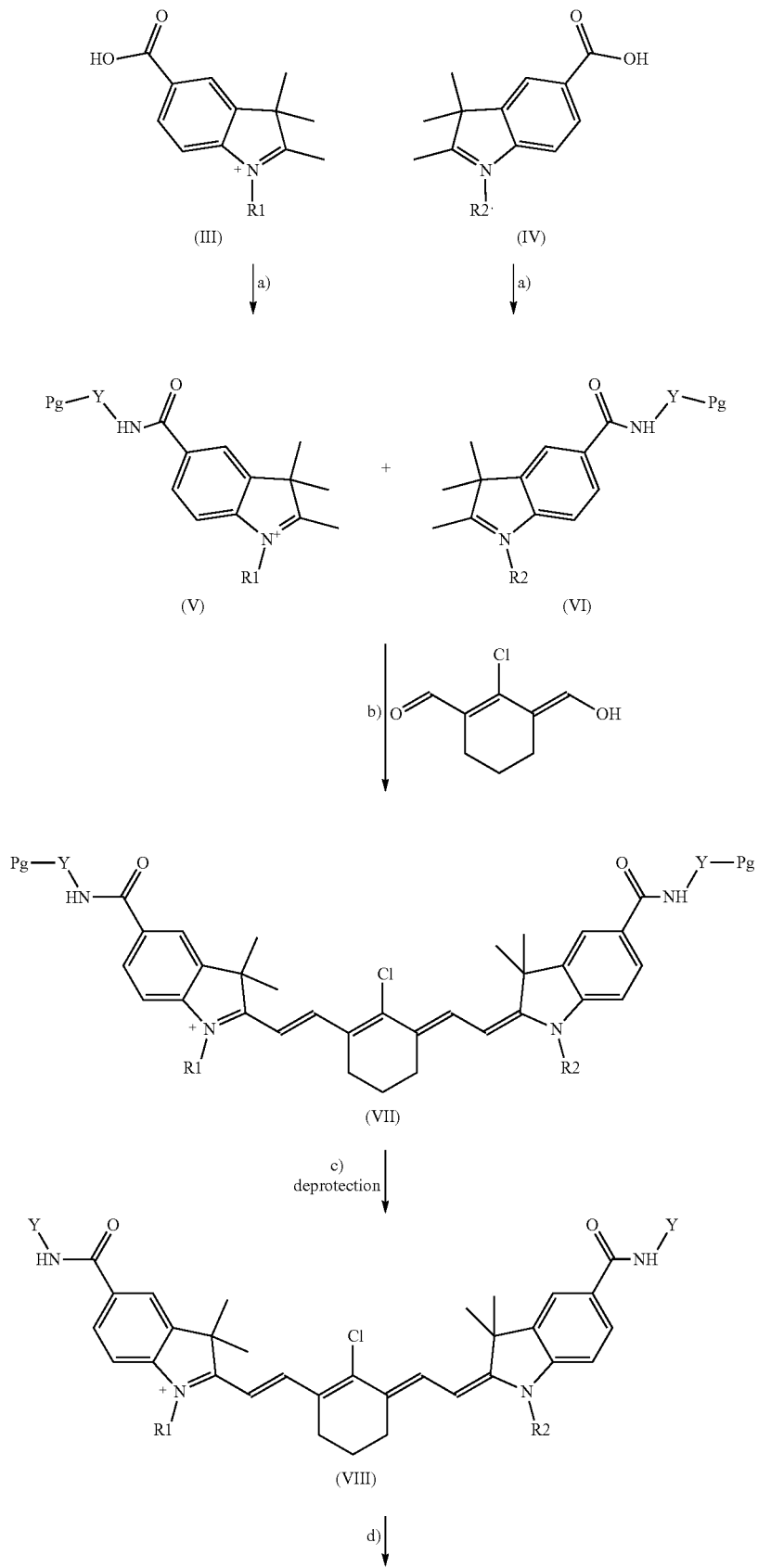

-continued

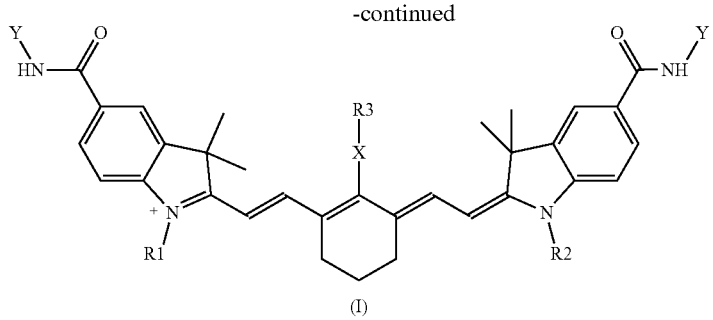

(I)

In the above Scheme 1, R1, R2, R3, X and Y are as defined above and Pg is absent or is a suitable protecting group.

Accordingly, a process of the present invention comprises the following steps:

a) treating suitable amounts of the 5-carboxy-2,3,3-trimethylindolenine of formula (III) and (IV) with a polyhydroxylated amine, such as for instance glucamine, meglumine, glucosamine, trometamol, serinol or isoserinol, bearing suitable protecting groups on the hydroxy moieties;

b) reacting the intermediate (V) and the intermediate (VI) obtained in steps a), together with 2-chloro-1-formyl-3-(hydroxymethylene)-1-cyclohexene, to obtain the cyanine intermediate of formula (VII), wherein R1, R2, Y and Pg are as defined;

c) optionally removing the protecting groups (Pg) of the Y groups from the intermediate (VII);

d) substituting the chloro atom on the intermediate (VII) with a suitable nucleophile to obtain the final product of formula (I) or a salt thereof.

According to step(s) a) the reaction of derivatives (III) and (IV) with the polyhydroxylated amine can be carried out by activation of the carboxylate group with a coupling agent, for instance selected from HATU, TBTU, HBTU, PyBOP, DCC, DSC and DCC-NHS, and an organic base, such as TEA, DIPEA, NMM or pyridine, in a solvent such as dimethylformamide, dimethylacetamide, dimethylsulfoxide, acetonitrile etc, at room temperature for a suitable time ranging from 30 minutes to several hours. This derivatization of the carboxylic acid can be performed on the alkylated indolenine or on the indole, prior quaternarization. In this case, it is important to protect the hydroxyl groups of the polyhydroxilated amines with a suitable protecting group such as acetyl, before the alkylation with sultone or bromohexanoic acid. This alkylation can be performed neat or in a high boiling solvent, such as butyrronitrile, sulfolane, 1,2-dichlorobenzene, dimethylacetamide, dimethylformamide or dimethylsulfoxide, stirring the solution at high temperature, for instance between 90° C. and 180° C., for several hours, typically from 12 hours to 5 days.

According to step b) the reaction can be performed using the Vilsmeier reagent in the bis anilido form or in the bis aldehyde form (as reported in Scheme 1). The reaction can be carried out in several solvents such as for example ethanol, methanol, acetic anhydride or acetic acid, with or without the addition of different bases, such as trimethylamine, pyridine, sodium acetate, potassium acetate etc., stirring the mixture at different temperatures ranging from 45° C. to 120° C. for several hours (typically 2-24 hours).

According to step c), any protecting group of intermediate (VII) is removed from the moieties Y according to the known procedures, described for instance in T. W. Green and P. G. M. Wuts, Protective Groups in Organic Synthesis, Wiley, N.Y. 2007, 4$^{th}$ Ed., Ch. 5. Differently from other classes of cyanines, these dyes showed higher stability at acidic pHs even at higher temperatures and several hours.

According to step d) the reaction can be performed using several protocols, depending on the X—R3 substituent. When phenol or its derivative such as phenol-SO$_3$H is introduced, the dye can be heated in DMSO in the presence of an inorganic base, such as sodium or potassium carbonate. Whereas, when the chloro is replaced by phenyl or its derivative, the reaction can be run in degassed water or a mixture of degassed water and a co-solvent, such as methanol, ethanol, etc., heating for shorter time in the presence of a Pd catalyst, such as Pd acetate or Pd tetrakys and optionally a base, such as sodium or potassium carbonate.

When R1 has the same meaning of R2, only one reaction a) is carried out and the subsequent step b) is performed with two units of intermediate (V) or (VI) instead of one unit of intermediate (V) and one unit of intermediate (VI).

Alternatively, when R1 has the same meaning of R2 and is a linear or branched C$_1$-C$_6$ alkyl substituted by —SO$_3$H, the compounds of formula (I) can be also prepared according to the following Scheme 2:

Scheme 2

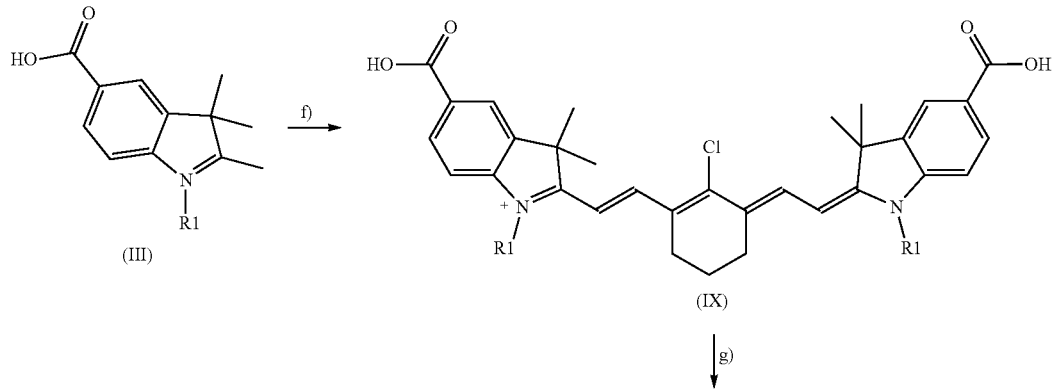

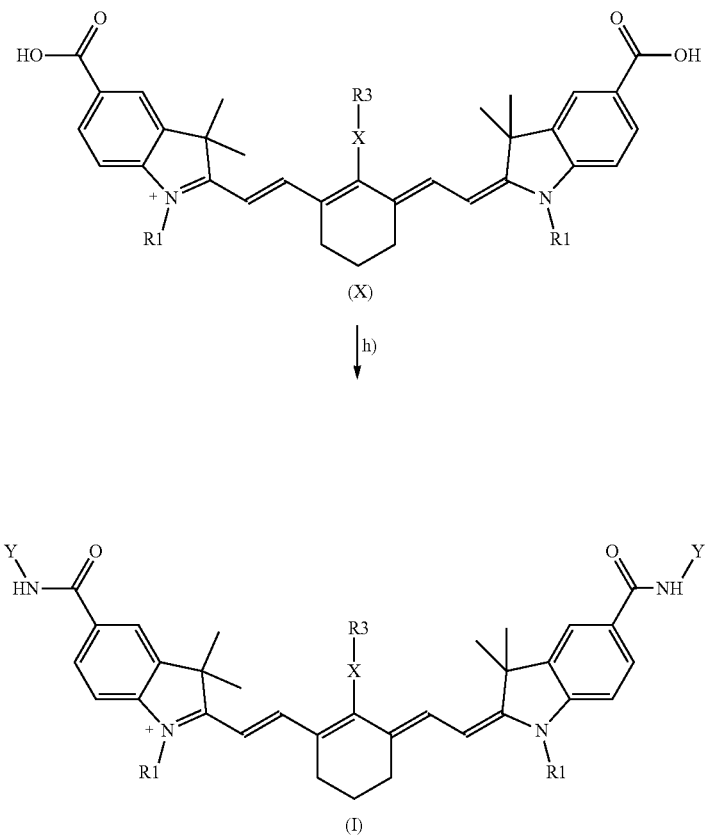

(X)

↓ h)

(I)

In the above Scheme 2, R1 is linear or branched $C_1$-$C_6$ alkyl substituted by —$SO_3H$ and X, Y and R3 are as defined above.

Accordingly, another process of the present invention comprises the following steps:

f) reacting at least two equivalent the indolenine intermediate (III), wherein R1 is linear or branched $C_1$-$C_6$ alkyl substituted by —$SO_3H$, with the Vilsmeier reagent (in the bis aldehydic or bis-anilido form) to obtain the corresponding cyanine intermediate of formula (IX);

g) substituting the chloro atom on the intermediate (IX) with a suitable nucleophile to obtain the intermediate (X);

h) treating suitable amounts of intermediate of formula (X) with a polyhydroxylated amine, such as for instance glucamine, meglumine, glucosamine, trometamol, serinol or isoserinol to obtain the final product of formula (I) or a salt thereof.

According to step f) the reaction can be carried out in several solvents such as for example ethanol, methanol, acetic anhydride or acetic acid, with or without the addition of different bases, such as trimethylamine, pyridine, sodium acetate, potassium acetate etc., stirring the mixture at different temperatures ranging from 45° C. to 120° C. for several hours (typically 2-24 hours).

According to step g) the reaction can be performed using several protocols, depending on the X—R3 substituent. When phenol or its derivative such as phenol-$SO_3H$ is introduced, the dye can be heated in DMSO in the presence of an inorganic base, such as sodium or potassium carbonate. Whereas, when the chloro is replaced by phenyl or its derivative, the reaction can be run in degassed water or a mixture of degassed water and a co-solvent, such as methanol, ethanol, etc., heating for shorter time in the presence of a Pd catalyst, such as Pd acetate or Pd tetrakys and optionally a base, such as sodium or potassium carbonate.

According to step h) the reaction of derivative (X) with the polyhydroxylated amine can be carried out by activation of the carboxylate group with a coupling agent, for instance selected from HATU, TBTU, HBTU, PyBOP, DCC, DSC and DCC-NHS, and an organic base, such as TEA, DIPEA, NMM or pyridine, in a solvent such as dimethylformamide, dimethylacetamide, dimethylsulfoxide, acetonitrile etc, at room temperature for a suitable time ranging from 30 minutes to several hours.

In a further embodiment, a compound of formula (I), prepared according to the processes of the invention, can be conveniently converted into another compound of formula (I) by operating according to well-known synthetic conditions, the following being examples of possible conversions:

e) converting a compound of formula (I) wherein R2 is —COOH, i.e. a compound of formula (Ib), into a corresponding compound of formula (I) wherein R2 is —$CONH_2$, i.e. a compound of formula (Ic):

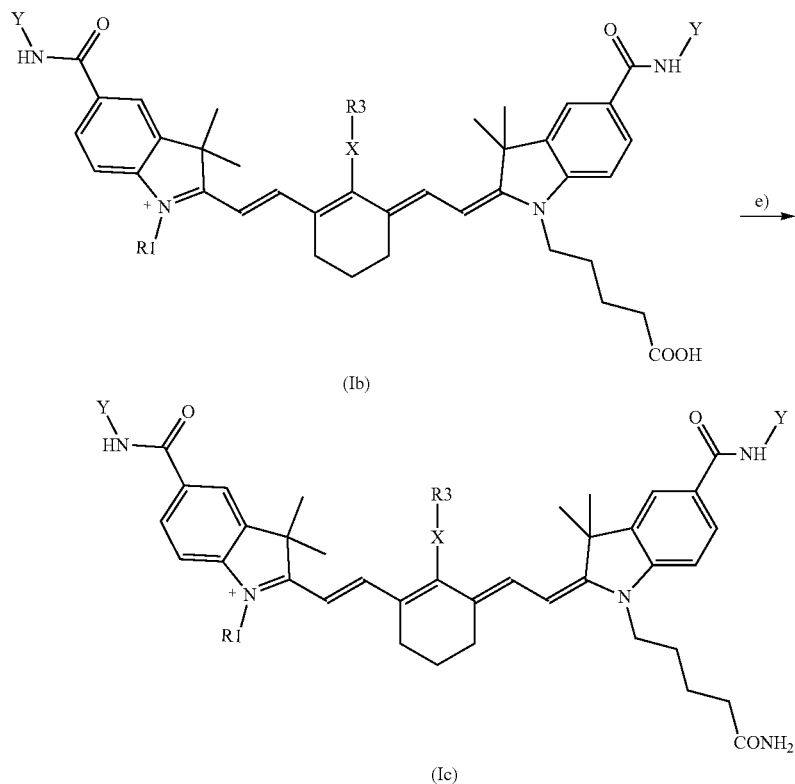

(Ib)

(Ic)

According to step e), the conversion of a carboxylic acid of formula (Ib) into the corresponding carboxamide of formula (Ic) can be accomplished in a variety of ways and experimental conditions, which are widely known in the art for preparation of carboxamides. As an example, the carboxylic acid can be first converted in a suitable activated ester and then reacted with an ammonium salt, such as NH$_4$Cl, preferably in the presence of a coupling agent, such as HBTU.

Preparation of Conjugate Compounds of Formula (II)

The cyanine derivatives of formula (I), or salts thereof, can be conjugated with a suitable targeting moiety, optionally with the insertion of a spacer, to obtain the corresponding compounds of formula (II). The conjugation can be accomplished following different procedures known in the art, such as for instance via direct coupling of a carboxylic acid group of the compounds with a nucleophilic residue of the targeting moiety, or optionally with the spacer, or by previous activation, wherein the carboxylic acid group is transformed in a more reactive group, e.g. an ester such as NHS, before the coupling.

In one embodiment, in case of activation of a carboxylic acid through formation of a NHS ester, the invention provides for a method of labelling a targeting moiety using a dye of formula (XIa)

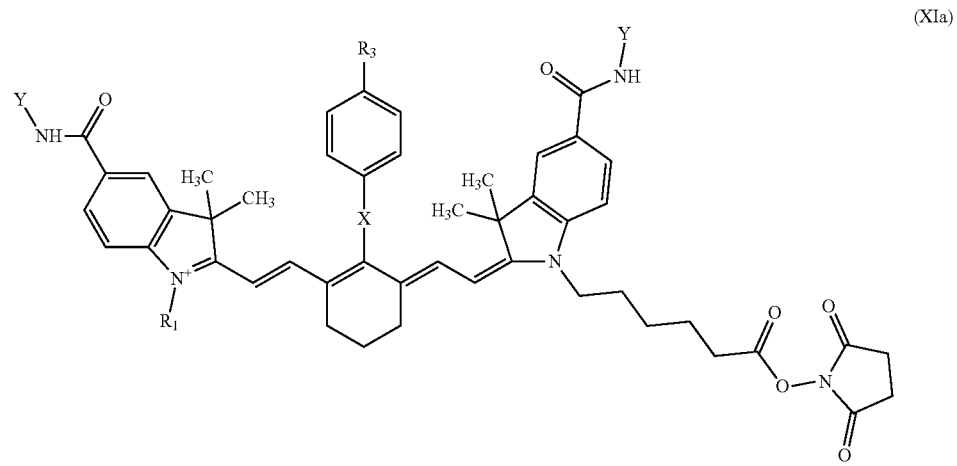

(XIa)

or a dye of formula (XIb)

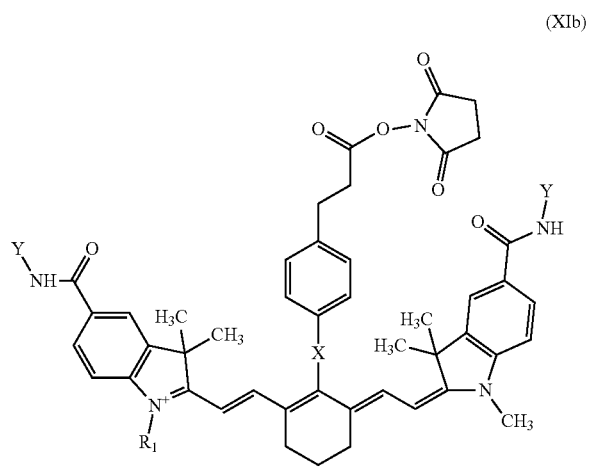

(XIb)

wherein
- X is direct bond or —O—; Y is a group selected from linear or branched $C_1$-$C_6$ alkyl, $C_3$-$C_7$ cycloalkyl and heterocyclyl, substituted by at least two hydroxyl groups;
- R1 is a linear or branched $C_1$-$C_6$ alkyl substituted by a group selected from —$SO_3H$, —COOH, —$CONH_2$ and —COO—$C_1$-$C_6$ alkyl; and
- R3 is hydrogen, —$SO_3H$ or a linear or branched $C_1$-$C_6$ alkyl substituted by —COOH or —CONH—Y, wherein Y is a group selected from linear or branched $C_1$-$C_6$ alkyl, $C_3$-$C_7$ cycloalkyl and heterocyclyl, substituted by at least two hydroxyl groups, the method comprising reacting the dye of formula (XIa) or (XIb) with the targeting moiety.

If a compound of the formula (I) or (II) prepared according to the processes described above is obtained as mixture of isomers, their separation using conventional techniques into the single corresponding isomer of the formula (I) or (II) is within the scope of the present invention.

The final compounds may be isolated and purified using conventional procedures, for example chromatography and/or crystallization and salt formation.

A compound of formula (I) or (II) as defined above can be coverted into a pharmaceutically acceptable salt. The compounds of formula (I) or (II) as defined above, or the pharmaceutically acceptable salt thereof, can be subsequently formulated with a pharmaceutically acceptable carrier or diluent to provide a pharmaceutical composition.

EXPERIMENTAL PART

The invention and its particular embodiments described in the following part are only exemplary and not to be regarded as a limitation of the present invention: they show how the present invention can be carried out and are meant to be illustrative without limiting the scope of the invention.

Materials and Equipment

All chemicals and solvents used for the reactions were reagent grade. Analytical grade solvents were used for chromatographic purifications. Most of the reagents, unless reported otherwise, are commercial products, including the targeting moieties (e.g. Panitumumab (Vectibix, Amgen;

CASNr: 339177-26-3); c(RGDfK) (Cyclo(Arg-Gly-Asp-D-Phe-Lys), Bachem; CAS Nr: 161552-03-0). All synthesized compounds were purified by reverse phase chromatography (RP-HPLC) and characterized by mass spectroscopy using a LC/MS instrument equipped with a UV-VIS detector and an ESI source. Analysis were performed with a Waters Atlantis dC18 5 μm, 4.6×150 mm column using a gradient of phase A $CH_3COONH_4$ 10 mM and phase B acetonitrile. Measured mass/charge ratios are listed for each compound.

A dual-beam UV-VIS spectrophotometer (Lambda 40, Perkin Elmer) was used to determine the absorbance (Abs) of the compounds of the invention. Emission/excitation (Em/Ex) spectra and absolute fluorescence quantum yield (4)) measurements were carried out on a spectrofluorometer (FluoroLog-3 1IHR-320, Horiba Jobin Yvon) equipped with an F-3018 integrating sphere accessory. The measurements were performed using an excitation wavelength at maximum absorbance of different dyes, and the sample was excited with a 450 W Xenon Light Source. Detection was performed by photomultiplier tubes (PMT-NIR) cooled detector or by TBX-04 detector. Dye solutions were carefully prepared to have an absorbance lower than 0.1 (optical densities) to minimize re-absorption phenomena.

In vivo imaging experiments were performed using the IVIS Spectrum In Vivo Imaging System (Perkin Elmer Inc.). The system is equipped with 10 narrow band excitation filters (30 nm bandwidth) and 18 narrow band emission filters (20 nm bandwidth) spanning 430-850 nm.

| | List of abbreviations |
|---|---|
| DCC | N,N'-dicyclohexylcarbodiimide |
| DIPEA | N,N-Diisopropylethylamine |
| DMF | Dimethylformamide |
| DMSO | Dimethyl sulfoxide |
| DSC | N,N'-Disuccinimidyl carbonate |
| EuK | Glutamic acid-urea-lysine |
| HATU | 1-[Bis(dimethylamino)methylene]-1H-1,2,3-triazolo[4,5-b]pyridinium 3-oxid hexafluorophosphate |
| HBTU | O-Benzotriazol-1-yl-N,N,N',N'-tetramethyluronium hexafluorophosphate |
| HPLC | High performance liquid chromatography |
| PBS | Phosphate buffered saline |
| NHS | N-hydroxysuccinimide |
| NMM | N-methylmorpholine |
| RT | Room temperature |
| PyBOP | (benzotriazol-1-yloxy)tripyrrolidinophosphonium hexafluorophosphate |
| TEA | Triethylamine |
| TBTU | 2-(1H-Benzotriazole-1-yl)-1,1,3,3-tetramethyluronium tetrafluoroborate |
| TSTU | O-(N-Succinimidyl)-1,1,3,3-tetramethyluronium tetrafluoroborate |
| μL | Microliter |
| μM | Micromolar |
| $t_R$ | Retention time (HPLC) |
| cRGDfK | Cyclo-(Arg-Gly-Asp-D-Phe-Lys) |

The abbreviations for individual amino acids residues are conventional: for example, Asp or D is aspartic acid, Gly or G is glycine, Arg or R is arginine. The amino acids herein referred to should be understood to be of the L-isomer configuration unless otherwise noted (for instance Phe or "f" of the c(RGDfK) is in the form of D-isomer, as indicated in the list of abbreviations).

Example 1: Synthesis of Compound 11

Preparation of Intermediate (Va)

5-carboxy-2,3,3-trimethyl-1-(4-sulfobutyl)-3H-indol-1-ium (10.8 g, 31.9 mmol) was suspended in dry DMF (100 mL) under N₂ atmosphere: D-Glucamine (6.9 g, 38.2 mmol), DIPEA (11 mL, 63.7 mmol) and HATU (14.5 g, 38.2 mmol) were added. The solution was stirred at RT for 16 hours, then cold diethyl ether (200 mL) was added. The mixture was filtered and the solid was washed with ethyl acetate (2×50 mL). The solid was dissolved in water and purified by flash chromatography on pre-packed C18 silica column with 0.1% ammonium acetate/acetonitrile gradient. Fractions containing pure product were combined, distilled under vacuum and freeze-dried three times, giving a pale pink solid (13.6 g, 80% yield) HPLC purity at 270 nm: 94%. MS: [M+H]$^+$ 504.2.

Preparation of Intermediate (VIIa)

Acetic acid (8.65 mL) was added to a suspension of intermediate (Va) (2.0 g, 3.98 mmol) in acetic anhydride (10 mL). The mixture was heated at 45° C. and 2-chloro-1-formyl-3-(hydroxymethylene)-1-cyclohexene (377.8 mg, 2.19 mmol) was added obtaining a yellow solution. The temperature was increased up to 75° C. (the solution became green-brown) and sodium acetate (408 mg, 4.97 mmol) was added obtaining immediately a green solution. The solution was stirred 3 hours at 100° C., then it was cooled down to RT and the solvents were removed under reduced pressure. The crude was dissolved in water-acetonitrile and purified by flash chromatography on pre-packed C18 silica column with a water-acetonitrile gradient. Fractions containing the pure product were combined and distilled under vacuum, giving a green solid (2.5 g, 40% yield). HPLC purity at 780 nm: 90%. MS: [M+H]$^+$ 1560.5.

Preparation of Intermediate (VIIIa)

Intermediate (VIIa) (2.5 g, 1.59 mmol) was dissolved in water/acetonitrile 1/1 (20 mL) and the pH was adjusted from 2.2 to 1.5 with 1N HCl. The solution was stirred at 80° C. for 16 hours. The crude was purified by flash chromatography on pre-packed C18 silica column with a water-acetonitrile gradient. Fractions containing the pure product were combined, distilled under vacuum and freeze-dried, obtaining a green solid (1.09 g, 60% yield). HPLC purity at 780 nm 95%. MS: [M+H]$^+$ 1140.7.

Synthesis of Compound 11

To a solution of Intermediate (VIIIa) (1.09 g, 0.95 mmol) in degassed water (20 mL), 4(2-carboxyethyl)-benzenboronic acid (332 mg, 1.71 mmol), Pd(PPh 3) 4 (165 mg, 0.14 mmol) and sodium carbonate (181 mg, 1.71 mmol) were added. The mixture was stirred at 80° C. under nitrogen atmosphere for 16 hours. Then, after cooling at RT, pH was adjusted to 6.5 with 2N HCl. The crude mixture was purified by flash chromatography on pre-packed C18 silica column with a water-acetonitrile gradient. Fractions containing the pure product were combined, distilled under vacuum and freeze-dried, obtaining a green solid (0.714 g, 60% yield). HPLC purity at 780 nm: 99%. MS: [M+H]$^+$ 1253.5.

Example 2: Synthesis of Compound 12

Compound 11 as prepared in example 1 (56 mg, 0.0434 mmol) was suspended in dry DMSO (5 mL) under nitrogen atmosphere. NMM (19 µL, 0.174 mmol), HATU (66 mg, 0.174 mmol) and D-glucamine (39 mg, 0.217 mmol) were added. After stirring 2 hours at RT, the mixture reaction was precipitated in cold ethyl acetate (30 mL), the green solid was dissolved in water and purified by flash chromatography on pre-packed C18 silica column with a 0.1% ammonium acetate-acetonitrile gradient. Fractions containing the product were combined, distilled under vacuum and freeze-dried three times, giving a green solid as ammonium salt (69.88 mg). In order to remove the ammonium counterions, the solid was dissolved in water, charged on a C18 cartridge and washed with water (2 CV), 0.1% HCOOH (2 CV), water (5 CV) and eluted with water/acetonitrile 1/1. Solvents were distilled under vacuum and freeze-dried, obtaining a green solid (37 mg, 60% yield). HPLC purity at 780 nm: 100%. MS: [M+H]$^+$ 1419.4.

Example 3: Synthesis of Compound 13

Preparation of Intermediate (VIb)

In a dried round bottom flask, 2,3,3-trimethyl-3H-indole-5-carboxylic acid (711 mg, 3.5 mmol) was solubilized in dry DMF (4 mL) under nitrogen atmosphere, then DIPEA (380 µL, 4.90 mmol) was added. After 30 minutes of stirring at RT, a solution of TBTU (603 mg, 4.20 mmol) in dry DMF (2 mL) was added. After 1 hour of stirring at RT, a suspension of D-glucamine (312 mg, 3.85 mmol) in dry DMF (2 mL) was added. After one night the reaction was not complete, therefore the same amount of TBTU, DIPEA and D-glucamine were added and stirred for other 2 hours. The mixture was dried under vacuum and purified on pre-packed C18 silica column with a water-acetonitrile gradient. Fractions containing the pure product were combined, distilled under vacuum and freeze-dried, obtaining a white-brown powder (888.2 mg, 70% yield). HPLC purity at 270 nm 93% purity, MS: [M+H]$^+$ 502.57.

Acetic anhydride (3 mL) and pyridine (0.5 mL) were added to this intermediate (888.2 mg, 2.42 mmol), resulting in a suspension that gradually solubilized during time. The mixture was kept under stirring in a nitrogen atmosphere at RT for 4 hours. The solution was concentrated under vacuum and purified on a pre-packed C18 silica column with a water-acetonitrile gradient. Fractions containing the pure product were collected, concentrated under vacuum and freeze-dried, obtaining a white-brown solid (861.4 mg, 62% yield). HPLC purity at 270 nm 97.5%, MS: [M+H]$^+$ 204.

In a round bottom flask, such obtained product (1.103 g, 1.91 mmol) and 1-bromohexanoic acid (933 mg, 4.77 mmol) were solubilized in 1,2-dichlorobenzene (6 mL). The mixture was heated at 130° C. under nitrogen atmosphere for 6 hours, then other 1-Bromohexanoic acid (933 mg, 4.77 mmol) was added and the reaction was kept at the same conditions overnight. The crude was washed with diethyl ether, the solvent was decanted, the solid was dissolved in acetonitrile and purified on pre-packed C18 silica column with a water-acetonitrile gradient. Fractions containing the product were collected and concentrated in vacuum, to give a red oil (861.4 mg, 62% yield). HPLC purity at 270 nm 97.5%, MS: [M+H]$^+$ 691.0.

Preparation of Intermediate (VIIb)

In a dried round bottom flask, intermediates (Va) (1.170 g, 2.33 mmol), prepared as in example 1, and (VIb) (1.79 g, 2.33 mmol) were suspended in acetic anhydride (20 mL) and acetic acid (5 mL). The mixture was heated at 45° C., until the two powders were fully solubilized. Then, 2-chloro-3-(hydroxymethylene)-1-cyclohexene-1-carboxaldehyde (430 mg, 2.49 mmol) was added and the mixture was heated up to 50° C. Potassium acetate (237 mg, 2.89 mmol) was added and the mixture was heated at 100° C. for 2 hours. The solvents were removed under vacuum and the crude green solid was purified on a pre-packed C18 silica column with a water-acetonitrile gradient. Fractions containing the product were collected, concentrated in vacuum and freeze-dried, to give a green powder (1.221 g, 35% yield). HPLC purity at 780 nm 72%, MS: [M+H]$^+$ 1540.6.

Preparation of Intermediate (VIIIb)

Intermediate (VIIb) (701 mg, 0.33 mmol) was solubilized in acetonitrile (3 mL) and water (15 mL) was added. The solution was acidified at pH 1.6 with 1N HCl and was heated at 80° C. for 4 hours, then at 55° C. overnight. The organic solvent was removed under reduced pressure and the aqueous solution was purified on a pre-packed C18 silica column with a water-acetonitrile gradient. Fractions containing the product were collected, concentrated under vacuum and freeze-dried to give a green powder (179 mg, 50% yield). HPLC purity at 780 nm 95%, MS: [M+H]$^+$ 1120.3.

Synthesis of Compound 13

In a dried round bottom flask, intermediate (VIIIb) (115 mg, 1.03 mmol) was solubilized in degassed water (3 mL), then phenylboronic acid (22.7 mg, 1.85 mmol), sodium carbonate (19.6 mg, 1.85 mmol) and palladium tetrakis (17.8 mg, 0.15 mmol) were added. The mixture was heated at 80° C. under nitrogen atmosphere for 2 hours. The solution was brought at pH 7.15 with 0.1 N HCl and purified on a pre-packed C18 silica column with a water-acetonitrile gradient. Fractions containing the product were collected, concentrated under vacuum and freeze-dried, giving a green powder (99 mg, 83% yield). HPLC purity at 780 nm 98%, MS: [M+H]$^+$ 1162.2.

Example 4: Synthesis of Compound 14

A solution of intermediate (VIIIb) prepared as in example 2 (120 mg, 0.107 mmol) in dry DMSO (5 mL) was dropped into a suspension of phenol (101 mg, 1.07 mmol) and anhydrous potassium carbonate (148 mg, 1.07 mmol) in dry DMSO (7 mL) under nitrogen atmosphere. The mixture was stirred at 50° C. for 4 hours. After cooling to RT, cold diethyl ether (30 mL) was added, the solid was filtered and washed twice with cold diethyl ether. It was dissolved in water and the pH was adjusted from 11.5 to 6 with 0.5 N HCl. The crude solid was purified by flash chromatography on pre-packed C18 silica column with a 0.1% ammonium acetate-acetonitrile gradient. Fractions containing the pure product were combined and distilled under vacuum. In order to remove the ammonium counterions pH was adjusted to 1.6, the product was charge on a C18 silica cartridge, washed with water and eluted with water-acetonitrile 1:1. Solvents were distilled under vacuum and the aqueous solution was freeze-dried giving a green solid (42 mg, 33% yield). HPLC purity at 780 nm 99.3%. MS: [M+H]$^+$ 1178.3.

Example 5: Synthesis of Compound 15

A solution of intermediate (VIIIb) prepared as in example 2 (20 mg, 0.018 mmol) in dry DMSO (3 mL) was dropped into a suspension of 4-hydroxybenzene sodium sulfonate (35 mg, 0.18 mmol) and anhydrous potassium carbonate (25 mg, 0.18 mmol) in dry DMSO (5 mL) under nitrogen atmosphere. The mixture was stirred at 50° C. for 4 days. Cold diethyl ether (30 mL) was added to the brown mixture, the solid was filtered and washed twice with cold diethyl ether. The solid was dissolved in water and pH was adjusted from 11.5 to 6 with 0.5 N HCl: the solution turned green again. The crude was purified by flash chromatography on pre-packed C18 silica column with a water-acetonitrile gradient. Fractions containing the pure product were combined, distilled under vacuum and freeze-dried giving a green solid (15 mg, 65% yield). HPLC purity at 780 nm 100%. MS: [M+H]$^+$ 1257.3.

Example 6: Synthesis of Compound 16

A solution of intermediate (VIIIa) prepared as in example 1 (30 mg, 0.026 mmol) in dry DMSO (3 mL) was dropped into a suspension of 4-hydroxybenzene sodium sulfonate (14 mg, 0.08 mmol) and anhydrous potassium carbonate (10 mg, 0.08 mmol) in dry DMSO (3 mL) under nitrogen atmosphere. The mixture was stirred at 80° C. for 6 hours. Cold ethyl acetate (20 mL) was added to the brown mixture, the solid was filtered, dissolved in water and pH was adjusted from 11.5 to 3 with 0.5 N HCl: the solution turned green again. The crude was purified by flash chromatography on pre-packed C18 silica column with a water-acetonitrile gradient. Fractions containing the pure product were combined, distilled under vacuum and freeze-dried giving a green solid (14 mg, 42% yield). HPLC purity at 780 nm 97.8%. MS: [M+H]$^+$ 1277.3.

Example 7: Synthesis of Compound 17

In a dried round bottom flask, intermediate (VIIIa) prepared as in example 1 (9 mg, 0.008 mmol) was solubilized in degassed water (2 mL), then phenylboronic acid (2.2 mg, 0.018 mmol) and palladium acetate (0.15 mg, 0.0006 mmol) were added. The mixture was refluxed under nitrogen atmosphere for 2 hours. The solution was purified on a pre-packed C18 silica column with a water-acetonitrile gradient. Fractions containing the product were collected, concentrated under vacuum and freeze-dried, giving a green powder (7 mg, 75% yield). HPLC purity at 780 nm 98%, MS: [M+H]$^+$ 1184.3.

Example 8: Synthesis of Compound 19

Preparation of Intermediate (IXa)

Compound (IIIa) (180 mg, 0.53 mmol), N-[(3-(anilinomethylene)-2-chloro-1-cyclohexen-1-Amethylene]aniline monohydrochloride (101 mg, 0.265 mmol) and sodium acetate (109 mg, 1.32 mmol) were dissolved in absolute ethanol (55 mL) and the solution was refluxed for 26 hours. The solvent was removed under reduced pressure and the crude was purified by flash chromatography on silica C18 column using a gradient of water/acetonitrile. Fractions containing the pure product were combined, distilled under vacuum and freeze-dried three times, obtaining a green solid (154 mg, 72% yield). HPLC purity at 780 nm 97%. MS: [M+H]$^+$ 815.2.

Preparation of Intermediate (Xa)

A solution of intermediate (IXa) (40 mg, 0.05 mmol) in dry DMSO (4 mL) was dropped into a suspension of phenol (45 mg, 0.49 mmol) and anhydrous potassium carbonate (68 mg, 0.49 mmol) in dry DMSO (8 mL) under nitrogen atmosphere. The mixture was stirred at 50° C. for 8 hours. After cooling to RT, cold diethyl ether (30 mL) was added, the solid was filtered and washed twice with cold diethyl ether. It was dissolved in water and the pH was adjusted from 12 to 6 with 0.5 N HCl. The crude solid was purified by flash chromatography on pre-packed C18 silica column with a water/acetonitrile gradient. Fractions containing the pure product were combined and distilled under vacuum. Solvents were distilled under reduced pressure and the aqueous solution was freeze-dried giving a green solid (26 mg, 61% yield). HPLC purity at 780 nm 98%. MS: [M+H]$^+$ 872.1

Synthesis of Compound 19

TBTU (5.1 mg, 0.015 mmol) was added to a solution of intermediate (Xa) (3.3 mg, 0.0038 mmol) and DIPEA (6 μL, 0.031 mmol) in anhydrous DMF (5 mL). The solution was stirred at RT for 30 minutes, then serinol (1 mg, 0.011 mmol) was added and the solution was stirred for 90 minutes. The solvent was removed under reduced pressure and the crude was purified by flash chromatography on silica C18 column eluting with a gradient of water-acetonitrile. Fractions containing the pure product were combined, concentrated under reduced pressure and freeze-dried, obtaining a darg green solid (2 mg, 53% yield). HPLC purity at 780 nm 98.5%. MS: [M+H]$^+$ 1019.1.

Analogously, the compounds 18, 20, 21, 22 and 23 were prepared by following a similar procedure, but using a different hydroxylated amine (as Y groups) or starting from a scaffold bearing a phenyl instead of phenol, as described above.

Example 9: Synthesis of Compound 1

Compound 11 (5 mg, 0.004 mmol) was dissolved in dry DMF (3 mL) under inert atmosphere. DIPEA (6.8 µL, 0.04 mmol) and TSTU (12 mg, 0.04 mmol) were added and the solution was stirred for 48 hours at RT. Then, cold diethyl ether (20 mL) was added and the precipitate was filtered and washed twice with cold diethyl ether, obtaining a green solid. HPLC purity at 780 nm: 90%. MS: [M+H]$^+$ 1351.

The NHS ester was dissolved in a solution of c(RGDfK) (2.7 mg, 0.004 mmol) in 1 mL of borate buffer at pH 9. The reaction was stirred for 24 hours at RT, then the product was precipitate in cold diethyl ether and washed twice with cold diethyl ether, obtaining a green solid. The crude solid was purified by HPLC chromatography on Kromasil C8 column using a linear gradient of 0.1% ammonium acetate/acetonitrile. Fractions containing the pure product were combined, distilled under vacuum and freeze-dried three times, obtaining a green solid (3.9 mg, 50% yield). HPLC purity at 780 nm: 97.6%. MS: [M+H]$^+$ 1840.6.

Example 10: Synthesis of Compound 3

Procedure A Via Direct Coupling

In a dry round bottom flask, compound 13 (2 mg, 0.0017 mmol) was solubilized in DMF (1 mL) with DIPEA (0.6 µl, 0.003 mmol) at RT under nitrogen flow. After 30 minutes of stirring at RT, a solution of TBTU (0.6 mg, 0.002 mmol) in dry DMF (1 mL) was added. After 1 hour of stirring at RT, a solution of c(RGDfK) (1.4 mg, 0.002 mmol) in dry DMF (1 mL) was dropped into the stirring solution. The reaction was stirred overnight at RT, then the solvent was removed under vacuum and the crude was purified on analytical HPLC C18 silica column with 0.1% ammonium acetate-acetonitrile gradient. Fractions containing the pure product were combined, concentrated under vacuum and freeze dried three times, obtaining a green powder (0.7 mg, 23% yield). HPLC purity at 780 nm 98%, MS: [M/2]$^+$ 872.8.

Procedure B Via NHS Ester

In a dry round bottom flask, compound 13 (5 mg, 0.0043 mmol) was solubilized in dry DMF (2 mL) with DIPEA (2.2 µl, 0.0129 mmol) and a solution of TSTU (3.78 mg, 0.0129 mmol) in dry DMF (1 mL) was added at room temperature under nitrogen flow. The green solution was stirred overnight at RT, then the product was precipitated by addition of cold diethyl ether. The solid was centrifuged, washed twice with diethyl ether and used in the following step with no further purification. The NHS ester was dissolved in a solution of c(RGDfK) (2.2 mg, 0.0043 mmol) in borate buffer at pH 9 (1 mL) and the solution was stirred at room temperature overnight. Then, pH was adjusted at 7 with 0.1 N HCl and the crude was purified on analytical HPLC C18 silica column with 0.1% ammonium acetate-acetonitrile gradient. Fractions containing the pure product were combined, concentrated under vacuum and freeze dried three times, obtaining a green powder (3.9 mg, 52% yield). HPLC purity at 780 nm 97.7%, MS: [M/2]$^+$ 872.8.

Example 11: Synthesis of Compound 2

Compound 15 (6 mg, 0.0048 mmol) was suspended in dry DMF (6 mL), then NMM (2.6 µL, 0.024 mmol) and TSTU (7.2 mg, 0.024 mmol) were added. The solution was stirred at RT for 16 hours. Cold diethyl ether (30 mL) was added, the precipitate was filtered and washed twice with cold diethyl ether. The green solid was used in the following step without any further purification, HPLC at 780 nm: 88%, MS: [M+H]$^+$ 1354.3.

The NHS ester was dissolved in borate buffer at pH 9 (1 mL) and a solution of c(RGDfK) (3.4 mg, 0.0048 mmol) in borate buffer at pH 9 (1 mL) was added. The solution was stirred at RT for 5 hours, then pH was adjusted to 6.5 with 0.1 N HCl and the crude was purified by HPLC chromatography on Phenyl-C18 column using a linear gradient of 0.1% ammonium acetate-acetonitrile. Fractions containing the pure product were combined, distilled under vacuum and freeze-dried three times, obtaining a green solid (6.4 mg, 71% yield). HPLC purity at 780 nm 99.6%. MS: [M+H]$^+$ 1845.5.

Example 12: Synthesis of Compound 4

Compound 14 (12 mg, 0.0102 mmol) was dissolved in dry DMF (1 mL) under nitrogen atmosphere. DIPEA (4.8 µL, 0.0286 mmol) and TBTU (4.6 mg, 0.0143 mmol) were added and after 1 hour of stirring at RT c(RGDfK) (6.15 mg, 0.0102 mmol) was added. The reaction was stirred at RT for 16 hours, then cold diethyl ether (25 mL) was added, the precipitate was filtered and washed twice with cold diethyl ether. The crude solid was dissolved in water and purified by HPLC chromatography on Phenyl-C18 column using a linear gradient of 0.1% ammonium acetate-acetonitrile. Fractions containing the pure product were combined, distilled under vacuum and freeze-dried three times, obtaining a green solid (12.3 mg, 67% yield). HPLC purity at 780 nm 98.3%, MS: [M+H]$^+$ 1763.6.

Example 13: Synthesis of Compound 5

The monoclonal antibody EGFR ligand Panitumumab (6 mg) was diluted up to 5 mg/mL in PBS and pH was adjusted by adding 120 µL of 1.0 M potassium phosphate pH 9. Compound 15-NHS ester (prepared as described for compound 2 in Example 11) was dissolved in DMSO at a concentration of 10 mg/ml; then the dye and the antibody were immediately mixed at a molar ratio of 2.5:1 and kept at room temperature in the dark for 3 h. After 3 h, the conjugation reaction mixture was layered onto phosphate buffered saline (PBS)-equilibrated Zeba Spin columns and centrifuged at 1500 g for 2 min to separate the conjugate from the free dye. After filtration through a 0.22-µm polyethersulfone (PES) membrane, the conjugated Panitumumab solution in PBS at pH 7.4 was analyzed by SE-HPLC, RP-HPLC, UV/VIS spectrophotometry to determine concentration and purity. The molar conjugation ratio (dyes molecules coupled per antibody) was 1.53.

Example 14: Synthesis of Compound 6

The small molecule CAIX ligand 4a, described in Wichert et al., Nat Chem 2015, 7, 241-249, was prepared according to the procedure therein disclosed and conjugated to compound 15. 11 mg of compound 15 (8.7 µmol) were dissolved in 1 mL of DMF, then 4.5 mg of PyBOP (8.7 µmol) and 6 µL of DIPEA (35.0 µmol) were added under continuous stirring. After 20 minutes, 8 mg of small molecule 4a (13.0 µmol) were dissolved in 1 mL of DMF and added to the reaction mixture which was stirred for additional 30 minutes at room temperature. Purification was performed by preparative HPLC with a yield of 50%. The isolated pure product was characterized by HPLC-UV-VIS-MS-ESI (+) using a Waters Atlantis dC18 column (µm, 4.6×150 mm). HPLC purity at 779 nm: 99%; MS: $[M/2]^+$ 929.7.

Example 15: Synthesis of Compound 7

The small molecule CAIX ligand 8a, described in Wichert et al., Nat Chem 2015, 7, 241-249, was prepared according to the procedure therein disclosed and conjugated to Compound 15. 9 mg of Compound 15 (7.1 µmol) were dissolved in 1 mL of DMF, then 3.7 mg of PyBOP (7.1 µmol) and 5 µL of DIPEA (28.0 µmol) were added under continuous stirring. After 20 minutes, 11 mg of molecule 8a (11.0 µmol) were dissolved in 1 mL of DMF and added to the reaction mixture which was stirred for additional 30 minutes at RT. The purification was performed by preparative HPLC with a yield of 50%. The isolated pure product was characterized by HPLC-UV-VIS-MS-ESI (+) using a Waters Atlantis dC18 column (µm, 4.6×150 mm).

HPLC purity at 780 nm: 99%; MS: $[M/2]^+$ 1157.8.

Example 16: Synthesis of Compound 8

9.9 mg of Compound 15 (7.9 µmol) was dissolved in 3 mL of dry DMF, then 2 µL of NMM (18.2 µmol) and 7.11 mg of TSTU (23.6 µmol) were added and the mixture was stirred for 2 h at RT. The NHS ester of Compound 15 (HPLC conversion 85.9%) was precipitated in 25 mL of ice cold ethyl acetate. The precipitate was washed with ethyl acetate and dried under $N_2$ flow.

The NHS ester of Compound 15 was dissolved in 1 mL of dry DMF. A solution prepared by dissolving 5.74 mg of EuK TFA salt (13.43 µmol) in 1 mL of DMF was dropped. Then, a solution of 13.72 µL DIPEA (7.8 µmol) in 1 mL DMF was dropped. The solution was allowed to stir overnight at RT under $N_2$ atmosphere. The product (HPLC conversion 84%) was precipitated in 25 mL of ice cold diethyl ether and purified on a pre-packed silica C18 column (BIOTAGE® SNAP ULTRA 26 g) with an automated flash chromatographic system (Combiflash Rf+) eluting with a water/acetonitrile gradient. Fractions containing the desired pure product were combined, concentrated under vacuum and freeze-dried, recovering 6.65 mg of a green solid (HPLC purity area %: 98.7% at 785 nm and 100% at 254 nm; $[M-H]^+$ 1558.7). The yield from Compound 15 was 54.0%.

Example 17: Synthesis of Compound 9

9.9 mg of Compound 15 (7.9 µmol) was dissolved in 3 mL of dry DMF. 2 µL of NMM (18.2 µmol) and 7.11 mg of TSTU (23.6 µmol) were added and the mixture was stirred for 2 h at RT. The NHS ester of Compound 15 (HPLC conversion 85.9%) was precipitated in 25 mL of ice cold ethyl acetate. The precipitate was washed with ethyl acetate and dried under $N_2$ flow.

NHS ester of Compound 15 was dissolved in dry DMF (1 mL). A solution of EuK-(3-(2-naphtyl)-alanine)-tranexamic acid TFA salt, prepared as described in Benešová et al., J Nucl Med 2015, 56: 914-920, (7.23 mg, 0.00945 mmol) in DMF (1 mL) was dropped. Then, a solution of DIPEA (6.86 µL, 0.039 mmol) in DMF (1 mL) was dropped. The solution was allowed to stir overnight at RT under $N_2$ atmosphere. The product (HPLC conversion 93%) was precipitated in 25 mL of ice cold diethyl ether and purified on a pre-packed silica C18 column (BIOTAGE® SNAP ULTRA 26 g) with an automated flash chromatographic system (Combiflash Rf+) eluting with a water/acetonitrile gradient. Fractions containing the desired pure product were combined, concentrated under vacuum and freeze-dried recovering 4.25 mg of a green solid (HPLC purity area %: 99.6% at 785 nm and 98% at 254 nm; $[M-H]^+$ 1894.6). The yield from Compound 15 was 28.0%.

Example 18: Optical Properties

The compounds of the invention have been characterized in terms of their optical properties in vitro in aqueous medium (i.e., water/PBS pH 7.4) and in a clinical chemistry control serum (Seronorm, Sero SA), mimicking the chemical composition and optical properties of human serum. All dye or dye-conjugate solutions were freshly prepared. ICG and S0456 were used as commercial references.

In particular, the excitation and emission maxima and the absolute fluorescence quantum yield (φ) of representative compounds of formula (I) and conjugates of formula (II) are shown in Table II.

TABLE II

Excitation/Emission maxima and absolute fluorescence quantum yields of compounds of formula (I) and (II)

| Dyes of formula (I) | Max Ex/Em (PBS pH 7.4) | Φ (PBS pH 7.4) | Φ (Seronorm) |
|---|---|---|---|
| ICG (Reference) | 780/810 nm | 1.5% | 7.8% |
| S0456 (Reference) | 782/803 nm | 3.9% | 7.7% |
| Compound 11 | 764/786 nm | 6.3% | 11.5% |
| Compound 14 | 781/803 nm | 4.4% | 10.6% |
| Compound 15 | 781/804 nm | 5.4% | 8.2% |
| Compound 17 | 768/788 nm | 5.5% | 11.8% |
| Compound 19 | 783/805 nm | 6.5% | 10.9% |
| Compound 18 | 781/804 nm | 6.2% | 10.5% |
| Compound 20 | 780/801 nm | 6.3% | 7.7% |
| Compound 21 | 769/790 nm | 5.6% | 12.8% |
| Compound 22 | 782/803 nm | 6.1% | 9.8% |
| Conjugates of formula (II) | Max Ex/Em (PBS pH 7.4) | Φ (PBS pH 7.4) | Φ (Seronorm) |
| Compound 1 | 771/788 nm | 4.4% | 10.9% |
| Compound 2 | 783/805 nm | 6.1% | 7.5% |
| Compound 3 | 771/787 nm | 6.4% | 8.1% |
| Compound 4 | 781/803 nm | 5.0% | 9.9% | n/a: not available

The compounds of the invention are characterized by absorption maxima comprised in the range from about 760 nm to 810 nm. The dyes are endowed with fluorescence emission in the near-infrared region and high fluorescence quantum yield, even when conjugated to a targeting moiety. Overall, the dyes and conjugates display higher fluorescence quantum yield than ICG and S0456.

Example 19: Affinity to Human Albumin (HSA)

An analysis of the binding affinity of the compounds of the invention to human albumin was carried out and the results compared with ICG and S0456 as a reference. Binding affinity to human serum albumin (HSA; Sigma Aldrich, A9511) was measured using two methods, according to the level of binding affinity of the compounds.

The first method, optimal for compounds which strongly interact with HSA, is based on the analysis of the absorbance spectrum peak shift after the incubation of the dye in solutions containing HSA. Briefly, the samples were incubated at a fixed concentration (1 µM) with HSA dilutions ($1\times10^{-6}$-$4\times10^{-4}$ M), in phosphate buffer for 5 min in the spectrophotometer at 25° C. before measurements. The measure was performed at the maximum absorbance wavelength of the shifted peak.

The second method, optimal for compound with low affinity for HSA, is based on measuring the variation of the absorbance of solutions containing the dye and various concentrations of HSA after ultrafiltration. Briefly, each compound was incubated at a fixed concentration (2 µM) with HSA dilutions ($1\times10^{-6}$-$4\times10^{-4}$ M), in phosphate buffer. The samples were centrifuged (10,000 g for 30 min at 25° C.) in a Microcon device (10 kDa MWCO, Amicon Ultra-0.5 Centrifugal Filter Unit with Ultracel-10 membrane, Millipore) and the absorbance measurements of the filtrates were obtained with the spectrophotometer at the maximum absorbance wavelength of the fluorophore.

For both methods, the affinity constant ($K_A$, $M^{-1}$) was calculated by fitting the raw data with the following formula:

$$\frac{\Delta A}{b} = \frac{\Delta \varepsilon \cdot K_{RL}[L] \cdot R_t}{K_{RL}[L] + 1}$$

wherein
$\Delta A/b$=Absorbance measured (b=1 cm)
$K_{RL}$=$K_A$ calculated by regression analysis (curve fitting)
$\Delta\varepsilon \cdot Rt$ calculated by regression analysis (curve fitting)
[L]=Albumin concentration In the first method, $\Delta A/b$ corresponds to the absorbance measured for each sample, whereas in the second method $\Delta A/b$ is obtained subtracting the absorbance of the control sample (dye without HSA) to the absorbance of each other sample.

Both methods have demonstrated to provide comparable results, as shown by parallel experiments conducted on the commercial cyanine dye IRDye 800CW carboxylate (LI-COR Inc., Lincoln, USA) using the first method (HSA $K_A$=215,000 $M^{-1}$) and the second method (HSA $K_A$=216,000 $M^{-1}$). However, the measurement of the affinity constant is more precise when the suitable method is used as a function of the affinity level of the compound.

The results of the binding affinity measured for representative compounds of the invention with one of the two methods are reported in Table III and compared with the results obtained for the cyanine dye IRDye 800CW carboxylate dye as reference compound.

TABLE III

| Binding affinity to human serum albumin (HSA) | |
|---|---|
| | HSA affinity ($K_A$, $M^{-1}$) |
| ICG (Reference) | 347,000 |
| S0456 (Reference) | 350,000 |
| Compound 11 | 6,500 |
| Compound 14 | 23,800 |
| Compound 15 | 90,600 |
| Compound 17 | 12,262 |
| Compound 18 | 14,600 |
| Compound 19 | 28,300 |
| Compound 20 | 13,800 |
| Compound 21 | 32,400 |

TABLE III-continued

| Binding affinity to human serum albumin (HSA) | |
|---|---|
| | HSA affinity ($K_A$, $M^{-1}$) |
| Compound 22 | 8,360 |
| Compound 2 | 26,200 |
| Compound 4 | 10,000 |

As shown in Table III, both the dyes and dyes-conjugates of the invention display a remarkably low binding affinity to human albumin compared to the known near-infrared dyes ICG and S0456, with affinity constants of one or two orders of magnitude lower.

This advantageous feature is preserved in the dyes of the invention even when conjugated with a targeting moiety (for instance Compounds 2 and 4), as the conjugation of the dyes with a targeting moiety does not affect the affinity to human albumin.

Example 20: Receptor Binding Affinity

The binding affinity of the conjugates of formula (II) to a specific receptor was determined to assess whether the targeting efficacy of the molecular vector is preserved after the labeling with the dyes of the invention.

As example of small molecules and peptide/peptidomimetic conjugates, the receptor affinity of representative integrin-binding conjugates was evaluated through calculation of their $IC_{50}$ (half maximal inhibitory concentration), using an enzyme-linked immunosorbent assay (ELISA), as previously reported (Kapp et al., Sci. Rep. 2017, 7, 39805).

Briefly, 96-well ELISA plates were coated overnight at 4° C. with the extracellular matrix (ECM) protein Vitronectin in carbonate buffer (15 mM $Na_2CO_3$, 35 mM $NaHCO_3$, pH 9.6). Each well was then washed with PBS-T-buffer (phosphate-buffered saline/Tween20, 137 mM NaCl, 2.7 mM KCl, mM $Na_2HPO_4$, 2 mM $KH_2PO_4$, 0.01% Tween20, pH 7.4) and blocked for 1 h at RT with TS-B-buffer (Tris-saline/BSA buffer; 20 mM Tris-HCl, 150 mM NaCl, 1 mM $CaCl_2$, 1 mM $MgCl_2$, 1 mM $MnCl_2$, pH 7.5, 1% BSA). In the meantime, a dilution series of the compound and internal standard was prepared in an extra plate. After washing the assay plate three times with PBS-T, 50 µL of the dilution series were transferred to each well. 50 µL of a solution of human recombinant integrin a $\alpha_v\beta_3$ (R&D Systems, 1 µg/mL) in TS-B-buffer was transferred to the wells and incubated for 1 h. The plate was washed three times with PBS-T buffer, and then primary antibody anti-$\alpha_v\beta_3$ was added to the plate. After incubation and washing three times with PBS-T, the secondary anti-IgG peroxidase-labeled antibody was added to the plate and incubated for 1 h. After washing the plate three times with PBS-T, the plate was developed by quick addition of 3,3',5,5'-tetrametylbenzidine (TMB) and incubated for 5 min in the dark. The reaction was stopped with 3 M $H_2SO_4$, and the absorbance was measured at 450 nm with a plate reader (Victor3, Perkin Elmer).

The $IC_{50}$ of the representative Compounds 1, 2 and 4 was tested in duplicate, and the resulting inhibition curves were analyzed using GraphPad Prism version 4.0 for Windows (GraphPad Software). The inflection point defines the $IC_{50}$ value. All experiments were conducted using c(RGDfK) as internal standard.

The tested molecular probes, coupled to c(RGDfK), showed comparable affinity to the human $\alpha_v\beta_3$ receptor, and similar affinity to the unconjugated reference peptidomimetic c(RGDfK), as reported in Table IV.

TABLE IV

Binding affinity to the human $\alpha_v\beta_3$ integrin receptor of compounds of formula (II) compared to the peptidomimetic c(RGDfK).

|  | Receptor affinity (IC$_{50}$, nM ± St. Dev.) |
| --- | --- |
| c(RGDfK) | 2.69 ± 0.70 |
| Compound 1 | 2.73 ± 0.50 |
| Compound 2 | 1.64 ± 0.41 |
| Compound 4 | 1.84 ± 0.38 |

Example 21: Cell Uptake

The human melanoma cell line VVM-266-4 (ATCC, CRL-1676) was used as in vitro model to assess the cell uptake of representative integrin-binding Compounds 1, 2 and 4, based on the high expression of the integrin receptors, particularly $\alpha_v\beta_3$, on the membrane of these cells (Capasso et al., PlosOne 2014).

Adherent cells at about 70% confluence were incubated with the Compounds 1 or 3 (1 pM) for 2 h at 37° C. (5% CO$_2$) in presence of Dulbecco's Modified Eagle's Medium (DM EM) supplemented with 10% FBS, 2 mM glutamine, 100 IU/mL penicillin and 100 µg/mL streptomycin. After two washing steps with PBS, cells were detached using 0.1 mM EDTA in PBS, centrifuged and suspended in buffer (PBS, 0.5% BSA, 0.1% NaN$_3$) for flow cytometry experiments. Fluorescence Activated Cell Sorting (FACS) was used to detect the fluorescence signal within the cells, as measure of cell uptake. Samples were excited with an Argon laser and the emission detected using a 670 nm longpass filter. Values of fluorescence intensity were obtained from the histogram statistic produced by the instrument software.

To assess the specificity of receptor-mediated cell uptake, experiments were performed by incubating the cells with the molecular probes in presence of high concentration (100 µM) of the unlabeled molecular vector c(RGDfK) as competitor. The residual internalization was calculated by considering the value of fluorescence intensity in absence of the competitor as 100%.

Furthermore, to assess the effect of biological fluids on the cell uptake, parallel experiments were performed incubating the cells with a compounds of the invention in presence of human serum from male AB plasma (Sigma Aldrich, H4522). The residual internalization was calculated by considering the value of fluorescence intensity in absence of the serum as 100%. Such uptake assessment also represents an indication of the percentage of compound which is sequestered by the plasma proteins when it diffuses through the vascular compartment before reaching the tissue of interest and the particular targeted receptor. In Table V the cell uptake performance of representative Compounds 2 and 4 of the invention is shown.

The present compounds displayed high cell uptake in presence of human serum. Thus, for the present compounds it is observed that the internalization in the cells is receptor-mediated and is only slightly affected by the binding to human serum proteins, in particular albumin (about 10-20% of residual uptake), confirming the medium-to-low binding affinity to human albumin of the present compounds ($K_A$=about 1-6×10$^3$ M$^{-1}$, as shown in example 10). Furthermore, the Compounds of the invention were compared with the reference compounds ICG-RGD (Capozza et al., Photoacoustic 2018, 11, 36-45) and ICG-c(RGDfK), prepared with the same method for ICG-RGD. These results show that the compounds of the present invention have been surprisingly found endowed with a higher efficacy in cell internalization with respect to similar compounds known in the art once incubated in presence of human serum.

TABLE V

Uptake of the integrin-binding fluorescent probes of the invention into WM-266-4 human melanoma cells.

|  | Residual cell uptake in presence of human serum |
| --- | --- |
| ICG-RGD | 12% |
| ICG-c(RGDfK) | 8% |
| Compound 2 | 90% |
| Compound 4 | 85% | n/a: not available.

Notably, neither the interaction of the present compounds with the receptor on the cell surface, nor the internalization of the receptor-probe complex within the cell were impaired by the structure of the conjugated dyes, and particularly by the presence in position Y of the compounds of moieties strongly hydrophilic and with high steric hindrance. Thus, the presence of the hydrophilic moieties on the conjugated dyes provide highly efficient and specific receptor binding and probe internalization even in presence of plasma proteins, which would sequester a conjugate lacking the hydrophilic moieties and negatively affect the binding efficiency.

Example 22: Tumor Uptake in Animal Models

Human Glioblastoma

Tumor uptake experiments were carried out in an animal model of human glioblastoma (subcutanous) overexpressing the integrin receptors, particularly $\alpha_v\beta_3$. Briefly, human glioblastoma U87MG cells (ATCC, HTB-14) were cultured in Eagle's Minimum Essential Medium (EMEM) supplemented with 10% Fetal Bovine Serum (FBS), 2 mM glutamine, 100 IU/mL penicillin, 100 µg/mL streptomycin. Male Balb/c nu/nu mice, 4-6 weeks of age (Charles River Laboratories), underwent subcutaneous implantation (right flank) of about 10 million cells suspended in 0.1 mL of EMEM. Mice were housed 4 per cage with food and water ad libitum. Animals were fed with VRF1 (P) sterile diet (Special Diets Services Ltd) up to the end of the acclimation period (5 days). Then, AIN-76a rodent diet irradiated (Research Diets), a special diet that reduces auto-fluorescence, was used up to the end of the experiments. Tumor growth was monitored by longitudinal assessments using a caliper up to the target size of 300-600 mm$^3$ (3-4 weeks after cell implantation). Imaging experiments were performed using the preclinical optical system IVIS Spectrum (Perkin Elmer).

In vivo imaging was performed under gas anesthesia (Sevofluorane 6-8% in oxygen). Animals were intravenously injected (lateral tail vein) with the compounds, and euthanized 24 h post-administration. Regions of interest (ROIs) were drawn on the excised tumor and healthy muscle tissues to evaluate signal intensity (expressed as Average Radiant Efficiency). The ratio between the fluorescence signal in the tumor and in the muscle (background tissue) was then calculated to assess the contrast.

The tumor-to-background ratio of representative Compounds 1 and 4 is displayed in Table VI. These results show a remarkably high tumor uptake, suggesting tumor-specific accumulation.

TABLE VI

Ex vivo tumor and excretory organs-to-muscle ratio 24 h
after administration of the Compounds 1 and 4 in
glioblastoma tumor bearing mice

| | Tumor-to-background ratio (n = 5/group), (mean ± St. Dev) |
|---|---|
| Compound 1 | 6.92 ± 0.64 |
| Compound 4 | 7.64 ± 0.86 |

Human Head and Neck Cancer

Tumor uptake experiments were performed in an animal model of human head and neck cancer (orthotopic), using Detroit-562 cells, overexpressing in particular integrin receptor $\alpha_v\beta_6$. Briefly, the human pharyngeal carcinoma cells Detroit-562 (ATCC, CCL-138) were cultured in Eagle's Minimum Essential Medium (EMEM) supplemented with 10% Fetal Bovine Serum (FBS), 2 mM glutamine, 100 IU/mL penicillin, 100 μg/mL streptomycin. Male Balb/c nu/nu mice, 4-6 weeks of age (Charles River Laboratories), underwent orthotopic implantation in the anterior portion of the tongue of about 2.5 million cells suspended in 0.03 mL di EMEM. Mice were housed 4 per cage with food and water ad libitum. Animals were fed with VRF1 (P) sterile diet (Special Diets Services Ltd) up to the end of the acclimation period (5 days). Then, AIN-76a rodent diet irradiated (Research Diets), a special diet that reduces auto-fluorescence, was used up to the end of the experiments. Tumor growth was monitored by longitudinal assessments using a caliper up to the target size of 10-20 mm$^3$ (7-10 days after cell implantation).

Imaging experiments were performed using the preclinical optical system IVIS Spectrum (Perkin Elmer). Animals were intravenously injected (lateral tail vein) with 3 nmol/mouse, at 24 hours post-administration were euthanized by anesthesia overdose, and the tongues were excised for ex vivo optical imaging. Regions of Interest (ROIs) were drawn on the anterior portion of the tongue (site of tumor cell implantation) and on the posterior region (healthy tissue) to derive the tumor-to-background ratio.

Ex vivo imaging performed 24 h after the administration of the Compounds 1 and 2 revealed a bright region in the tongue site of implantation of the tumor cells. Differently, the healthy region in the back of the tongue showed low signal, suggesting a low retention in healthy tissue. The administration of the compounds of the invention reveals the location of the tumor with moderate (TBR ~2) tumor-to-background contrast, as shown in Table VII.

TABLE VII

Ex vivo IVIS mean tumor-to-background ratio (TBR) 24 h
after administration of Compunds 1 and 2 in H&N
tumor bearing mice.

| | Tumor-to-background ratio (n = 5/group), (mean ± St. Dev) |
|---|---|
| Compound 1 | 2.27 ± 0.50 |
| Compound 2 | 2.26 ± 0.10 |

Human Colorectal Cancer

Tumor uptake experiments were performed in an animal model of human colorectal cancer (subcutaneous), using HT-29 cells, expressing low levels of integrin receptors. Briefly, the human colorectal adenocarcinoma cells HT-29 (ATCC, HTB-38) were cultured in McCoy's 5 A medium supplemented with 10% foetal bovine serum, 2 mM glutamine, 100 IU/mL penicillin and 100 μg/mL streptomycin. Male Athymic nude mice, 4-6 weeks of age (Envigo), underwent subcutaneous implantation (right flank) of about 5 million cells suspended in 0.1 mL of serum-free medium. Mice were housed 4 per cage with food and water ad libitum. Animals were fed with VRF1 (P) sterile diet (Special Diets Services Ltd) up to the end of the acclimation period (5 days). Then, AIN-76a rodent diet irradiated (Research Diets), a special diet that reduces auto-fluorescence, was used up to the end of the experiments. Tumor growth was monitored by longitudinal assessments using a caliper up to the target size of 300-600 mm$^3$ (3-4 weeks after cell implantation). Imaging experiments were performed using the preclinical optical system IVIS Spectrum (Perkin Elmer).

In vivo imaging was performed under gas anesthesia (Sevofluorane 6-8% in oxygen). Animals were intravenously injected (lateral tail vein) with the compounds of interest, and euthanized after 24 h post-administration. Regions of interest (ROIs) were drawn on the excised tumor and healthy reference tissue (muscle) to evaluate signal intensity (expressed as Average Radiant Efficiency).

The ratio between the fluorescence signal in the tumor and in the muscle (background tissue) was then calculated to assess the tumor-to-background ratio (TBR).

As shown in Table VIII, the representative Compounds 1 and 2 showed moderate tumor-to-background ratio (TBR ~4), allowing to clearly delineate the tumor tissue from the healthy background.

TABLE VIII

Ex vivo tumor-to-backround ratio (mean, SD, n = 5) 24 h
after administration of Compounds 1 and 2 in colorectal
cancer bearing mice.

| | Tumor-to-background ratio (n = 5/group), (mean ± St. Dev) |
|---|---|
| Compound 1 | 4.30 ± 1.50 |
| Compound 2 | 4.20 ± 0.80 |

REFERENCES

1. Cherrick et al., J Clin Invest 1960; 39(4): 592-600
2. Onda N. et al., Int J Cancer 2016; 139: 673-682
3. Tummers Q. et al., PlosOne 2015; 10(6): e0129766
4. Achilefu S. et al, J Med Chem 2002; 45: 2003-2015
5. Fidel J. et al., Cancer Res. 2015; 15; 75(20): 4283-4291
6. Hogstins C. et al., Clin Cancer Res 2016; 22(12): 2929-38
7. WO2002/024815
8. WO2007/136996
9. WO2004/065491
10. WO2015/114171
11. Wada H. et al, Chemical Engineering Journal 2018, 340 (3): 51-57
12. Vendrell M. et al, Organic & Biomolecular Chemistry 2011, 9 (13): 4760-4762
13. T. W. Green and P. G. M. Wuts, Protective Groups in Organic Synthesis, Wiley, N.Y. 2007, 4$^{th}$ Ed., Ch. 5
14. Kapp et al., Sci Rep, 2017; 7:3905
15. EP3636635 A1
16. Benešová et al., J Nucl Med 2015, 56: 914-920
17. Wichert et al., Nat Chem 2015; 7: 241-249
18. Li et al., FASEB J 2005; 19:1978-85
19. Williams et al., Chem Biol Drug Des 2018; 91: 605-619
20. Mujumdar R. B. et al., Bioconjugate Chem. 1993; 4(2): 105-111
21. Yamana et al, Chem. Pharm. Bull., 1972; 20(5): 881-891
22. Capozza et al., Photoacoustic 2018; 11: 36-45

The invention claimed is:
1. A compound of formula (II)

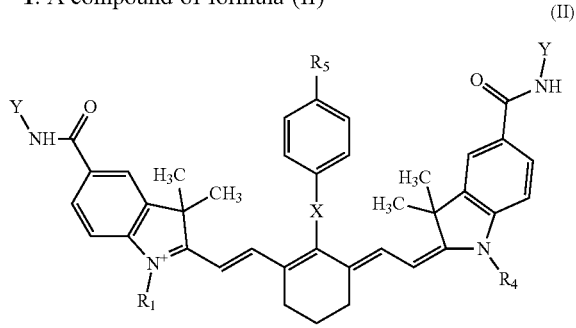

(II)

wherein
X is direct bond or —O—;
Y is a group selected from linear or branched $C_1$-$C_6$ alkyl, $C_3$-$C_7$ cycloalkyl and heterocyclyl, substituted by at least two hydroxyl groups;
R1 is linear or branched $C_1$-$C_6$ alkyl substituted by a group selected from —$SO_3H$, —COOH, —$CONH_2$ and —COO—$C_1$-$C_6$ alkyl;
R4 is linear or branched $C_1$-$C_6$ alkyl substituted by a group selected from —$SO_3H$, —COOH and —CONH—$(S)_m$-T, wherein
S is a spacer;
T is a targeting moiety interacting with an integrin receptor and comprising the sequence Arg-Gly-Asp; and
m is an integer equal to 0 or 1; and
R5 is selected from hydrogen, —$SO_3H$, a linear or branched $C_1$-$C_6$ alkyl substituted by —COOH or —CONH—Y, and a group CONH—$(S)_m$-T, wherein Y, S, T and m are defined above;
and wherein at least one between R4 and R5 is linear or branched $C_1$-$C_6$ alkyl substituted by CONH—$(S)_m$-T, or a stereoisomer or pharmaceutically acceptable salt thereof.

2. The compound of formula (II) according to claim 1, wherein S is selected from —$(CH_2)_p$COO—, —$CH_2CH_2O)_p$$CH_2CH_2$COO— and —$(CH_2CH_2O)_p$$CH_2CH_2$NH—, wherein p is an integer between 0 and 20.

3. The compound of formula (II) according to claim 1, represented by the formula (IIa)

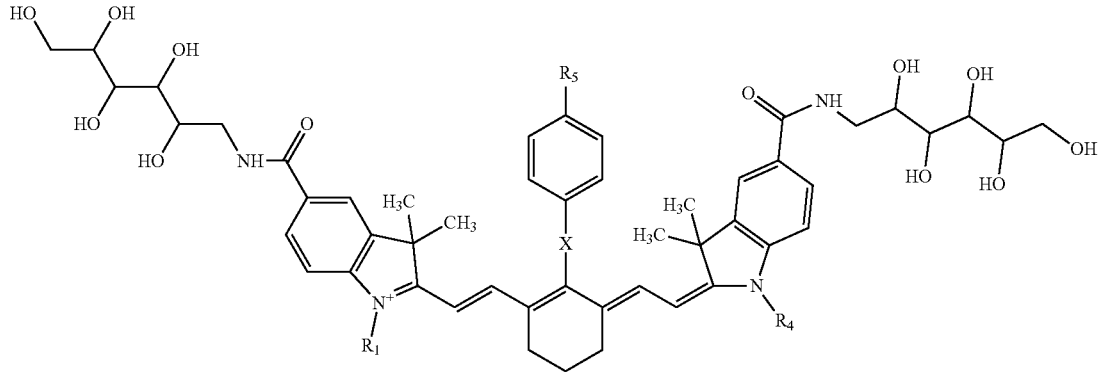

(IIa)

wherein R1, R4, R5 and X are as defined in claim 1.

4. The compound of formula (II) according to claim 3 which is selected from

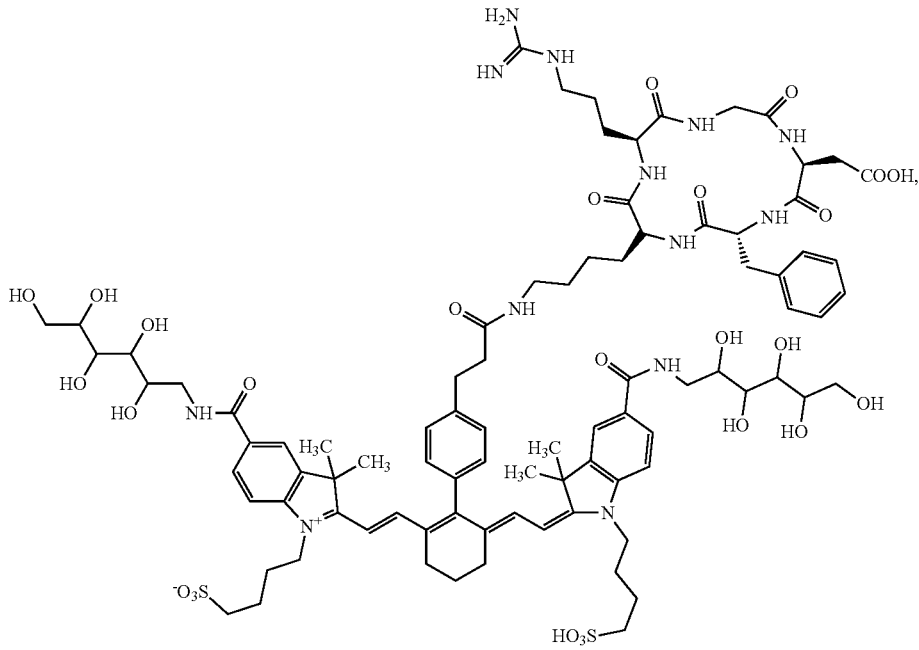

-continued
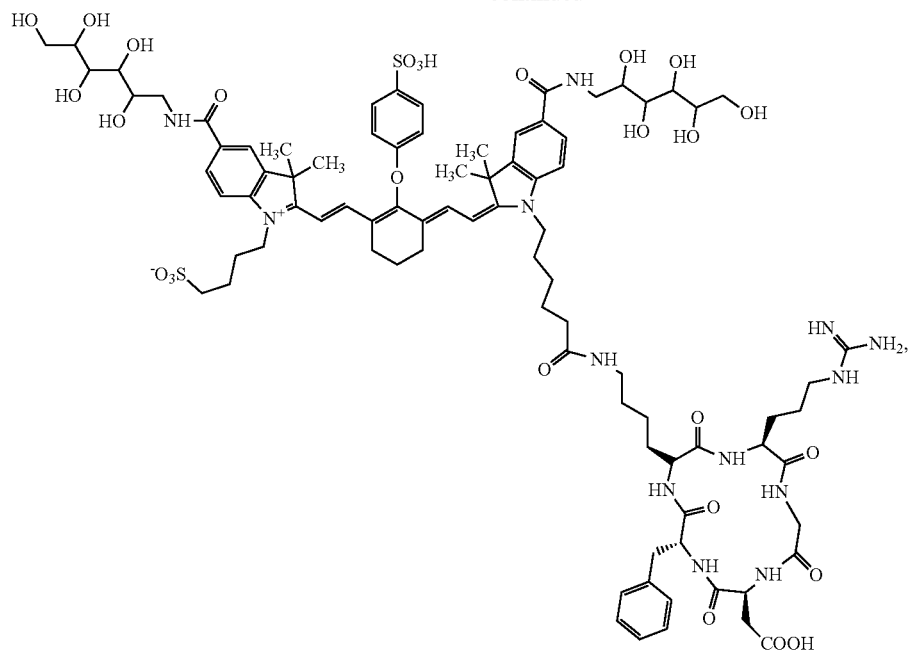
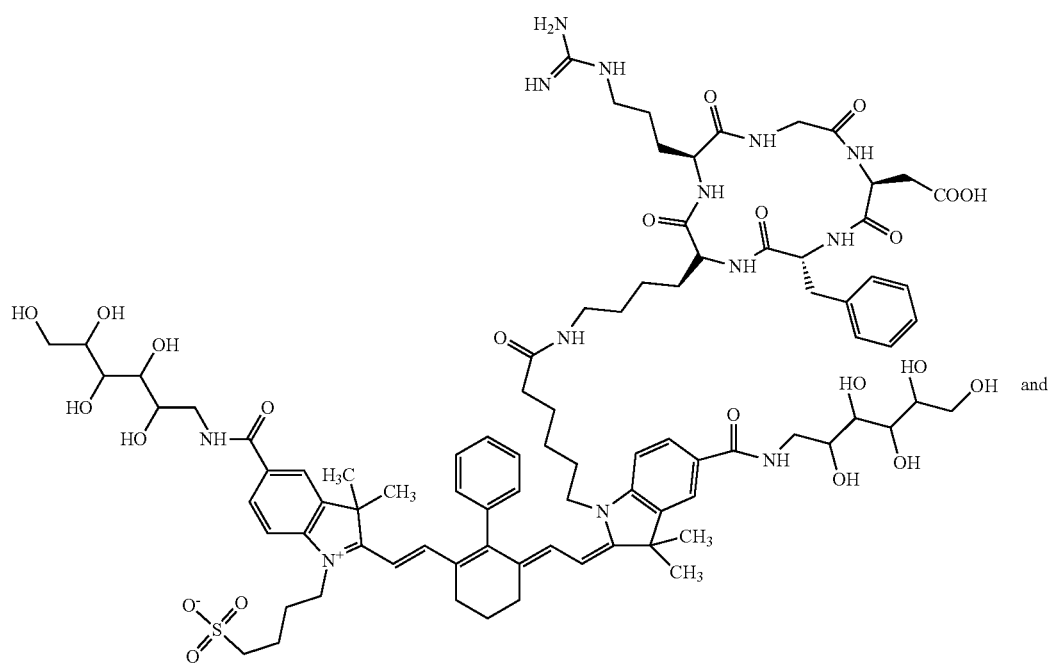

-continued

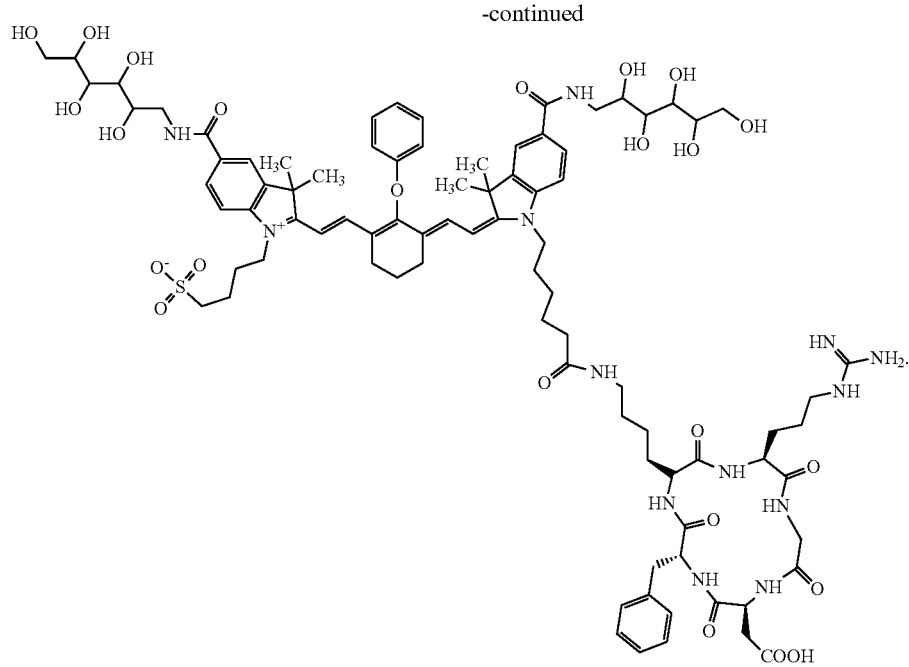

5. A method of biomedical optical imaging comprising:
contacting cells or tissues of a mammal with the compound as defined in claim 1;
irradiating the cells or tissues at a wavelength absorbed by the compound; and
detecting the near-infrared emission using a fluorescence camera.

6. The method according to claim 5 wherein the biomedical optical imaging is selected from the group consisting of angiography, perfusion imaging, bile duct imaging and nerve imaging.

7. The method according to claim 5, further comprising demarcating a tumor margin.

8. A pharmaceutical diagnostic composition comprising a compound as defined in claim 1 and at least one pharmaceutically acceptable carrier or excipient.

9. Diagnostic kit comprising at least one compound as defined in claim 1 together with one or more adjuvants.

* * * * *